United States Patent
Adams et al.

(10) Patent No.: US 6,380,238 B1
(45) Date of Patent: Apr. 30, 2002

(54) INDOLINE DERIVATIVES AS 5-HT$_{2B}$ AND OR 5-HT$_C$ RECEPTOR LIGANDS

(75) Inventors: David Reginald Adams; Jonathan Mark Bentley; Jonathan Richard Anthony Roffey; Richard John Hamlyn; Suneel Gaur; Matthew Alexander James Duncton; David Bebbington; Nathaniel Julius Monck; Claire Elizabeth Dawson; Robert Mark Pratt; Ashley Roger George, all of Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/786,154

(22) PCT Filed: Sep. 1, 1999

(86) PCT No.: PCT/GB99/02879

§ 371 Date: Mar. 1, 2001

§ 102(e) Date: Mar. 1, 2001

(87) PCT Pub. No.: WO00/12475

PCT Pub. Date: Mar. 9, 2000

(30) Foreign Application Priority Data

Sep. 1, 1998 (GB) .............................. 9819033

(51) Int. Cl.$^7$ ...................... C07D 209/08; A61K 31/40
(52) U.S. Cl. ........................ 514/415; 548/483
(58) Field of Search ........................ 548/483; 514/415

(56) References Cited

U.S. PATENT DOCUMENTS 5,755,829 A    5/1998   Terranova et al. .............. 8/409

FOREIGN PATENT DOCUMENTS

EP       0 780 118       6/1997
WO       95/32967        12/1995

OTHER PUBLICATIONS

G.A. Kennett, 5–HT$_{1C}$ Receptors and Their Therapeutic Relevance, *Current Drugs LTD ISSN 0967–8298*, 1993, pp. 317–362.

N. Upton, Studies on the Role of 5–HT$_{2C}$ and 5–HT$_{2B}$ Receptors in Regulating Generalised Seizure Threshold in Rodents, *European Journal of Pharmacology 359*, Oct. 1998, pp. 33–40.

G. Redmond, Mood Disorders in the Female Patient, *Int. Journal of Fertil*, 42(2), 1997, pp. 67–72.

J. Valentine et al., Differential Involvement of Serotonin 2A/C and Thromboxane A$_2$/Prostanoid Receptors in High–vs. Low–Shear Rate Arterial Thrombisis in Rabbits, *The Journal of Pharmacology and Experimental Therapeutics*, 1997, pp. 761–769.

L. Kubin et al., Serotonergic Excitatory Drive to Hypoglossal Motoneurons in the Decerebrate Cat, *Neuroscience Letters*, 139, 1992, pp. 243–248.

*Primary Examiner*—Robert Gerstl
(74) *Attorney, Agent, or Firm*—Foley & Lardner

(57) ABSTRACT

For use in therapy a chemical compound of formula (I),

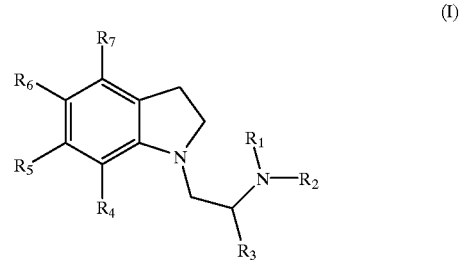

wherein $R_1$ to $R_3$ are independently selected from hydrogen and alkyl; $R_4$ to $R_7$ are independently selected from hydrogen, halogen, hydroxy, alkyl, aryl, heterocyclyl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, wherein at least one of $R_4$ to $R_7$ is a substituent group other than hydrogen, and pharmaceutically acceptable salts and prodrugs thereof, particularly for the treatment of disorders of the central nervous system; damage to the central nervous system; cardiovascular disorders; gastrointestinal disorders; diabetes insipidus, and sleep apnea, and especially for the treatment of obesity; chemical compounds of formula (I) other than compounds wherein $R_7$ is hydroxy.

23 Claims, No Drawings

INDOLINE DERIVATIVES AS 5-HT$_{2B}$ AND OR 5-HT$_C$ RECEPTOR LIGANDS

The present invention relates to indoline derivatives, to processes and intermediates for their preparation, to pharmaceutical compositions containing them and to their medicinal use. The active compounds of the present invention are useful in treating obesity and other disorders.

It has been recognised that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$, and obesity as a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, *Psychopharmacol.*, 1988, 96, 93–100; G. A. Kennett, C. T. Dourish and G. Cuzon, *Eur. J. Pharmacol.*, 1987, 141, 429–435) and to accelerate the appearance of the behavioural satiety sequence (S. J. Kitchener and C. T. Dourish, *Psychopharmacol.*, 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., *Psychopharmacol.*, 1994, 116, 120–122) and decreased the appetite and body weight of obese male and female subjects during subchronic treatment for a 14 day period (P. A. Sargeant et al., *Psychopharmacol.*, 1997, 133, 309–312). The anorectic action of mCPP is absent in 5-HT$_{2C}$ receptor knockout mutant mice (L. H. Tecott et al., *Nature*, 1995, 374, 542–546) and is antagonised by the 5-HT$_{2C}$ receptor antagonist SB-242084 in rats (G. A. Kennett et al., *Neuropharmacol.*, 1997, 36, 609–620). It seems therefore that mCPP decreases food intake via an agonist action at the 5-HT$_{2C}$ receptor.

Other compounds which have been proposed as 5-HT$_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethylpyrazole derivatives bind to 5-HT$_{2C}$ receptors and may be used in the treatment of obesity. WO-A-98130548 discloses aminoalkylindazole compounds as 5-HT$_{2C}$ agonists for the treatment of CNS diseases and appetite regulation disorders.

It is an object of this invention to provide selective, directly acting 5HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

According to the present invention there is provided for use in therapy a chemical compound of formula (I):

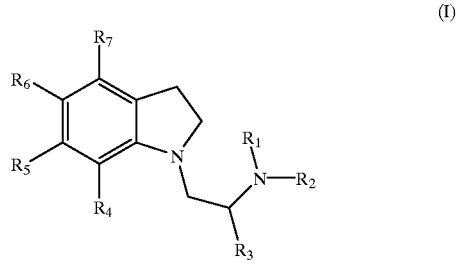

(I)

wherein:

R$_1$ to R$_3$ are independently selected from hydrogen and alkyl;

R$_4$ to R$_7$ are independently selected from hydrogen, halogen, hydroxy, alkyl, aryl, heterocyclyl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylanrinocarbonyl, dialkylaminocarbonyl, alkoxycarbonylamino, arninocarbonyloxy, monoalkylaminocarbonyloxy, dialkylaminocarbonyloxy, monoalkylaminocarbonylamino and dialkylaminocarbonylamino, wherein at least one of R$_4$ to R$_7$ is a substituent group other than hydrogen, and pharmaceutically acceptable salts and prodrugs thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably C$_3$ to C$_{12}$, more preferably C$_5$ to C$_{10}$, more preferably C$_5$, C$_6$ or C$_7$. Where acyclic, the alkyl group is preferably C$_1$ to C$_{10}$, more preferably C$_1$ to C$_6$, more preferably methyl, ethyl, propyl (n-propyl or isopropyl) or butyl (n-butyl, isobutyl or tertiary-butyl), more preferably methyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl, or a heteroaromatic group containing one or more, preferably one, heteroatom, such as pyridyl, pyrrolyl, faranyl and thienyl.

As used herein the term "heterocyclyl" means a saturated 4, 5, 6 or 7-membered ring preferably a 5 or 6-membered ring) containing 1, 2 or 3 heteroatoms (preferably 1 or 2 heteroatoms) selected from O, S and N (preferably from O and N).

The alkyl, aryl and heterocyclyl groups may be substituted or unsubstituted. Where substituted, there will generally be 1 to 3 substituents present, preferably 1 substituent. Substituents may include:

carbon-containing groups such as
alkyl,
aryl,
arylalkyl (e.g. substituted and unsubstituted phenyl, substituted
and unsubstituted benzyl);
halogen atoms and halogen-containing groups such as

| haloalkyl | (e.g. trifluoromethyl); |
|---|---| oxygen-containing groups such as

| alcohols | (e.g. hydroxy, hydroxyalkyl, aryl(hydroxy)alkyl), |
|---|---|
| ethers | (e.g. alkoxy, aryloxy, alkoxyalkyl, aryloxyalkyl), |
| aldehydes | (e.g. carboxaldehyde), |
| ketones | (e.g. alkylcarbonyl, alkylcarbonylalkyl, arylcarbonyl, arylalkylcarbonyl, arylcarbonylalkyl), |
| acids | (e.g. carboxy, carboxyalkyl), |
| acid derivatives such as esters | (e.g. alkoxycarbonyl, alkoxycarbonylalkyl, alkylcarbonyloxy, alkylcarbonyloxyalkyl), |
| amides | (e.g. aminocarbonyl, mono- or di-alkylaminocarbonyl, aminocarbonylalkyl, mono- or di-alkylaminocarbonylalkyl, arylaminocarbonyl), |
| carbamates | (e.g. alkoxycarbonylamino, aryloxycarbonylamino, aminocarbonyloxy, mono- or di-alkylaminocarbonyloxy, arylaminocarbonyloxy) |
| and ureas | (e.g. mono- or di-alkylaminocarbonylamino or arylaminocarbonylamino); | nitrogen-containing groups such as

| amines | (e.g. amino, mono- or di-alkylamino, aminoalkyl, mono- or di-alkylaminoalkyl), |
|---|---|
| azides, | |
| nitriles | (e.g. cyano, cyanoalkyl), |
| nitro; | | sulfur-containing groups such as
thiols, thioethers, sulfoxides and sulfones
(e.g. alkylthio, alkylsulfinyl, alkylsulfonyl,
alkylthioalkyl, alkylsulfinylalkyl,
alkylsulfonylalkyl, arylthio, arylsulfinyl,
arylsulfonyl, arylthioalkyl, arylsulfinylalkyl,
arylsulfonylalkyl);

and heterocyclic groups containing one or more, preferably one, heteroatom,
(e.g. thienyl, furanyl, pyrrolyl, imidazolyl,
pyrazolyl, thiazolyl, isothiazolyl, oxazolyl,
oxadiazolyl, thiadiazolyl, aziridinyl, azetidinyl,
pyrrolidinyl, pyrrolinyl, imidazolidinyl,
imidazolinyl, pyrazolidinyl, tetrahydrofuranyl,
pyranyl, pyronyl, pyridyl, pyrazinyl, pyridazinyl,
piperidyl, hexahydroazepinyl, piperazinyl,
morpholinyl, thianaphthyl, benzofuranyl,
isobenzofuranyl, indolyl, oxyindolyl, isoindolyl,
indazolyl, indolinyl, 7-azaindolyl, benzopyranyl,
coumarinyl, isocoumarinyl, quinolinyl,
isoquinolinyl, naphthridinyl, cinnolinyl,
quinazolinyl, pyridopyridyl, benzoxazinyl,
quinoxalinyl, chromenyl, chromanyl,
isochromanyl, phthalazinyl and carbolinyl).

As used herein, the term "alkoxy" means alkyl-O— and "alkoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical.

As used herein the term "prodrug" means any pharmaceutically acceptable prodrug of the compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiuric, tartaric, oxalic, p-toluenesulfonic and the like. Particularly preferred are fumaric, hydrochloric, hydrobromic, phosphoric, succinic, suliric and methane-sulfonic acids. Acceptable base salts include alkali metal (e.g. sodium, potassium), alkaline earth metal (e.g. calcium, magnesium) and aluminium salts.

Preferably, the compounds of formula (I) are selected from compounds in which $R_1$ is the same as $R_2$. Preferably, $R_1$ and $R_2$ are both hydrogen. In an embodiment of the invention, $R_1$ is hydrogen and $R_2$ is substituted or unsubstituted alkyl, preferably lower alkyl, preferably methyl. Where substituted, the substituent group is preferably an aryl group, preferably phenyl, pyridyl or thienyl.

Preferably, the compounds of formula (I) are selected from compounds in which $R_3$ is alkyl, preferably lower alkyl, preferably methyl. Where $R_3$ is alky, the carbon atom to which $R_3$ is attached is an asymmetric carbon atom. It is preferred that this asymmetric carbon atom is in the (S)-configuration, wherein the stereochemical assignment is defined with respect to a compound wherein $R_3$ is an unsubstituted alkyl group.

$R_4$ to $R_7$ are independently selected from hydrogen, halogen, hydroxy, alkyl (including cycloalkyl, halo-alkyl (such as trifluoromethyl) and arylalkyl), aryl, heterocyclyl (including aziridinyl, azetidinyl, pyrrolidinyl, piperidinyl, piperazinyl, morpholinyl, hexahydroazepinyl, tetrahydrofuranyl, tetrahydropyranyl, dioxanyl, tetrahydrothienyl and tetrahydrothiopyranyl), alkoxy (including arylalkoxy), aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylarninocarbonyloxy, dialkylaminocarbonyloxy, monoalkylaminocarbonylamino and dialkylaminocarbonylamino, wherein at least one of $R_4$ to $R_7$ is other than hydrogen.

In an embodiment of the invention $R_4$ to $R_7$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, alkylsulfoxyl and alkylsulfonyl, wherein at least one of $R_4$ to $R_7$ is other than hydrogen.

It is preferred that the compounds of formula (I) are selected from compounds in which $R_4$ is selected from halogen (preferably fluoro) and hydrogen. $R_4$ is preferably hydrogen.

It is preferred that the compounds of formula (I) are selected from compounds in which $R_5$ is selected from halogen, alkyl, aryl, alkoxy, alkylthio, monoalkylamino and dialkylamino. Preferably $R_5$ is selected from halogen, alkyl, alkoxy, alkylthio, monoalkylamino and dialkylamino, and more preferably from halogen (preferably chloro, bromo and fluoro, more preferably chloro and bromo), alkyl (preferably haloalkyl and more preferably trifluoromethyl), alkoxy (preferably lower alkoxy) and alkylthio (preferably lower alkylthio).

It is preferred that the compounds of formula (I) are selected from compounds in which $R_6$ is selected from halogen and hydrogen. Preferably $R_6$ is selected from halogen (preferably fluoro, chloro and bromo, and more preferably fluoro).

It is preferred that the compounds of formula (I) are selected from compounds in which $R_7$ is hydrogen.

In a preferred embodiment, the compounds of formula (I) are selected from 1-(6-chloro-5-fluoroindol-1-yl)-2-propylarnine, 1-(5,6-difluoroindolin-1-yl)-2-propylamine, 1-(6-bromo-5-fluoroindolin-1-yl)-2-propylamine, 1-(6-bromoindolin-1-yl)-2-propylamine, 1-(6-chloroindolin-1-yl)-2-propylamine, 1-(5-fluoro-6-trifluoromethylindolin-1-yl)-2-propylamine, 1-(5-fluoro-6-methylthioindolin-1-yl)-2-propylamine, 1-(5-fluoro-6-iodoindolin-1-yl)-2-propylamine, 1-(5-fluoro-6-ethylthioindolin-1-yl)-2-propylamine, 1-(-5-fluoro-6-methylindolin-1-yl)-2-propylamine, 1-(6-methylthioindolin-1-yl)-2-propylamine, 1-(6-ethylthioindolin-1-yl)-2-propylamine, 1-(6-trifluoromethylindolin-1-yl)-2-propylamine, 1-(6-methoxyindolin-1-yl)-2-propylamine, 1-(6-propylthioindolin-1-yl)-2-propylamine, 1-(6-isopropylthioindolin-1-yl)-2-propylamine, 2-(6-chloroindolin-1-yl)-1-ethylamine, 2-(6-bromoindolin-1-yl)-1-ethylamine, 1-(5-chloroindolin-1-yl)2-propylamine, 1-(5-fluoroindolin-1-yl)-2-propylamine and 1-(6-methylindolin-1-yl)-2-propylamine, and particularly the (S)-enantiomers thereof.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis.

In a preferred embodiment of the invention, a compound of formula (I) is in the form of its (S)-enantiomer, substantially free of its (R)-enantiomer. As used herein, the term "substantially free of its (R)-enantiomer" means that a composition comprising a compound of formula (I) contains a greater proportion of the (S)-enantiomer of the compound of formula (I) in relation to the (R)-enantiomer of the compound of formula (I). In a preferred embodiment of the present invention, the term "substantially free of its (R)-enantiomer", as used herein, means that the composition contains at least 90% by weight of the (S)-enantiomer and 10% by weight or less of the (R)-enantiomer. In a further preferred embodiment, the term "substantially free of its (R)-enantiomer" means that the composition contains at least 99% by weight of the (S)-enantiomer and 1% or less of the (R)-enantiomer. In another preferred embodiment, the term "substantially free of its (R)-enantiomer" means that the composition contains 100% by weight of the (S)-enantiomer. The above percentages are based on the total amount of a compound of formula (I) present in the composition.

According to a further aspect of the invention, there is provided a compound of formula (I), per se, wherein $R_7$ is a substituent other than hydroxy. In a preferred embodiment, there is provided a compound of formula (I), per se, wherein $R_7$ is hydrogen.

The compounds of formula (I) may be used in the treatment (including prophylactic treatment) of disorders associated with 5-$HT_2$ receptor function. The compounds may act as receptor agonists or antagonists. Preferably, the compounds may be used in the treatment (including prophylactic treatment) of disorders associated with 5-$HT_{2B}$ and/or 5-$HT_{2C}$ receptor function. Preferably, the compounds may be used in the treatment (including prophylactic treatment) of disorders where a 5-$HT_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment (including prophylaxis) of the above-mentioned disorders. In a preferred embodiment, there is provided use of a compound of formula (I) in the manufacture of a medicament for the treatment (including prophylaxis) of obesity.

According to a further aspect of the invention, there is provided a method of treatment (including prophylaxis) of a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I).

Compounds of formula (I) may be prepared according to Reaction Scheme 1 below. $R_1$ to $R_7$ are as previously defined. The (indolyl)-alkylethanol (III) may be prepared by reaction of the substituted indole (II) with an alkylene oxide in the presence of a strong base such as sodium hydride in a solvent such as tetrahydrofuran. The corresponding azido derivative (V) can be formed in a two step procedure from the derivative (III) by formation of the mesylate (IV), obtained by reaction of (III) with methanesulfonyl chloride in the presence of a base such as triethylamine, and subsequent treatment of the mesylate (IV) with sodium azide in a solvent such as dimethyl formamide. The indoline (VI) can then be obtained by reduction of the indole (V) with, for example, sodium cyanoborohydride in acetic acid as solvent. The resultant azidoindoline (VI) can then be reduced to a compound of formula (I) ($R_1=R_2=H$) using for example a mixture of zinc powder and nickel chloride hexahydrate in a solvent such as tetrahydrofuran or alternatively using hydrogen over a catalyst such as platinum(IV)oxide in a solvent such as ethanol.

Reaction Scheme 1

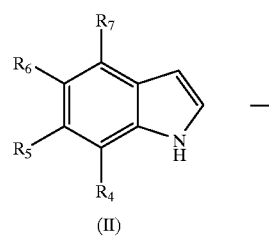

(II)

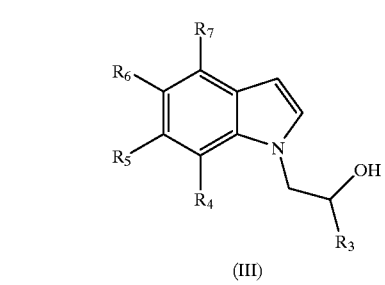

(III)

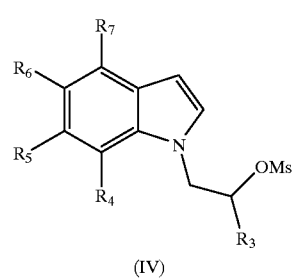

(IV)

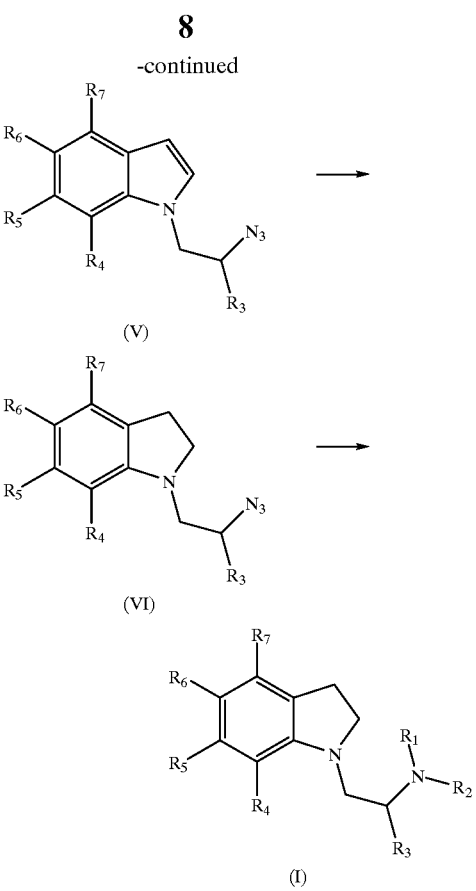

Alternatively compounds of the invention may be prepared according to Reaction Scheme 2 below. The carbamate (VII) may be formed by reaction of the indole (II) with a carbamoylethylsulfonate in the presence of a strong base such as potassium hydroxide in a solvent such as methyl sulfoxide. The indoline (VIII) may be obtained by reaction of the indole (VII) with a reducing agent such as sodium cyanoborohydride or a tetra-alkylammonium borohydride. The compounds of formula (I) ($R_1=R_2=H$) may be prepared by deprotection of the amine function of the indoline (VIII).

Reaction Scheme 2

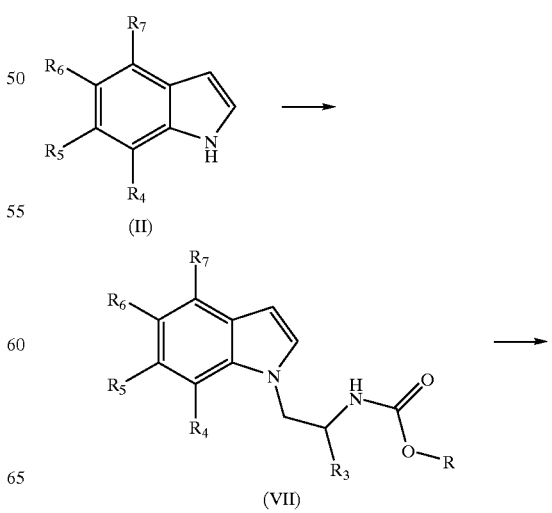

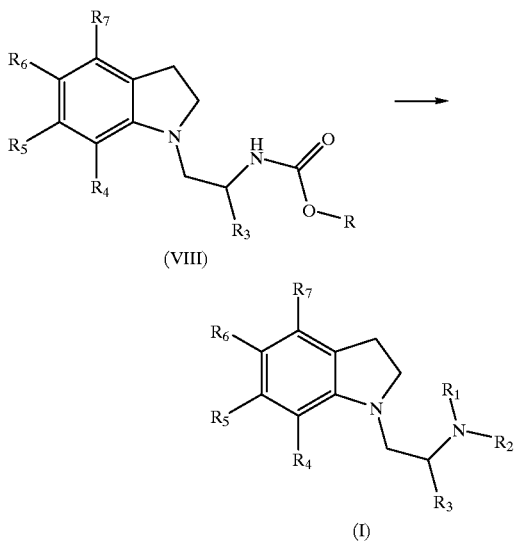

If, in any of the other processes mentioned herein, the substituent group $R_4$, $R_5$, $R_6$ or $R_7$ is other than the one required, the substituent group may be converted to the desired substituent by known methods. The substituents $R_4$, $R_5$, $R_6$ or $R_7$ may also need protecting against the conditions under which the reaction is carried out. In such a case, the protecting group may be removed after the reaction has been completed.

The compounds of formula (I) ($R_1$ and/or $R_2$=alkyl) may be prepared from compounds of formula (I) ($R_1$=$R_2$=H) by standard methods such as reductive alkylation with an appropriate aldehyde or ketone in the presence of a reducing agent such as sodium triacetoxyborohydride, formic acid or sodium cyanoborohydride.

The processes described above may be carried out to give a compound of the invention in the form of a free base or as an acid addition salt. If the compound of the invention is obtained as an acid addition salt, the free base can be obtained by basifiing a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions comprising a compound of formula (I) may be formulated in a conventional manner using one or more pharmaceutically acceptable carriers. Thus, the active compounds of formula (I) may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of formula (I) may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of formula (I) may also be formulated in rectal compositions such as suppositories or retention enemas, e.g., containing conventional suppository bases such as cocoa butter or other glycerides.

For intranasal administration or administration by inhalation, the active compounds of formula (I) are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of formula (I) for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

EXPERIMENTAL

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the 5-$HT_{2C}$ receptor the 5-$HT_{2C}$ receptors were radiolabeled with [$^3$H]-5-HT. The affinity of the compounds for 5-HT$_{2C}$ receptors in a CHO cell line was determined according to the procedure of D. Hoyer, G. Engel and H. O. Kalkman, *European J. Pharmacol.*, 1985, 118, 13–23.

Method (b): For the binding to the 5-HT$_{2B}$ receptor the 5-HT$_{2B}$ receptors were radiolabeled with [$^3$H]-5-HT. The affinity of the compounds for human 5-HT$_{2B}$ receptors in a CHO cell line was determined according to the procedure of K. Schmnuck, C. Ullmer, P. Engels and H. Lubbert, *FEBS Lett.*, 1994, 342, 85–90.

Method (c): For the binding to the 5-HT$_{2A}$ receptor the 5-HT$_{2A}$ receptors were radiolabeled with [$^{125}$I]-DOI. The affinity of the compounds for 5-HT$_{2A}$ receptors in a CHO cell line was determined according to the procedure of D. J. McKenna and S. J. Peroutka, *J. Neurosci.*, 1989, 9, 3482–90.

The thus determined activity of compounds of formula (I) is shown in Table 1.

TABLE 1

| Compound | K$_i$ (2C) | K$_i$ (2B) | K$_i$ (2A) |
| --- | --- | --- | --- |
| Example 1 | 357 nM | 113 nM | 405 nM |
| Example 10 | 55 nM | 138 nM | 252 nM |
| Example 12 | 77 nM | 42 nM | 1092 nM |
| Example 13 | 122 nM | 175 nM | 461 nM |
| Example 22 | 260 nM | 92 nM | 325 nM |
| Example 24 | 235 nM | 148 nM | 1866 nM |
| Example 25 | 63 nM | 22 nM | 156 nM |
| Example 26 | 1156 nM | 761 nM | 1262 nM |
| Example 50 | 61 nM | 159 nM | 332 nM |
| Example 51 | 165 nM | 140 nM | 1113 nM |

2. Functional Activity

The functional activity of compounds of formula (I) was assayed using a Fluorimetric Imaging Plate reader (FLIPR). CHO cells expressing the human 5-HT$_{2C}$ or human 5-HT$_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 μL/well of assay buffer (Hanks balanced salt solution containing 20 mM Hepes and 2.5 mM probenecid). The drug (dissolved in 50 μL of the assay buffer) was added at a rate of 70 μL/sec to each well of the FLIPR 96 well plate during fluorescence measurements. The measurements were taken at 1 sec intervals and the maximum fluorescent signal was measured (approx 10–15 secs after drug addition) and compared with the response produced by 10 μM 5-HT (defined as 100%) to which it was expressed as a percentage response (relative efficacy). Dose response curves were constructed using Graphpad Prism (Graph Software Inc.).

The thus determined activity of compounds of formula (I) is shown in Table 2.

TABLE 2

| Compound | EC$_{50}$ (nM) | h5-HT$_{2A}$ Relative Efficacy (%) | EC$_{50}$ (nM) | h5-HT$_{2C}$ Relative Efficacy (%) |
| --- | --- | --- | --- | --- |
| Example 2 | 1000 | 63 | 100 | 77 |
| Example 9 | 5600 | 52 | 253 | 89 |
| Example 10 | 2215 | 49 | 125 | 62 |
| Example 12 | 2409 | 49 | 230 | 59 |
| Example 13 | 386 | 72 | 75 | 74 |
| Example 14 | 3700 | 55 | 2120 | 71 |
| Example 15 | 10000 | 12 | 4700 | 14 |
| Example 16 | 793 | 52 | 9 | 80 |
| Example 17 | 7500 | 40 | 616 | 76 |

TABLE 2-continued

| Compound | EC$_{50}$ (nM) | h5-HT$_{2A}$ Relative Efficacy (%) | EC$_{50}$ (nM) | h5-HT$_{2C}$ Relative Efficacy (%) |
| --- | --- | --- | --- | --- |
| Example 18 | — | 7 | 870 | 27 |
| Example 19 | — | 21 | 3800 | 34 |
| Example 20 | — | 17 | 750 | 68 |
| Example 22 | 2567 | 57 | 83 | 87 |
| Example 23 | 1351 | 34 | 354 | 76 |
| Example 24 | 3651 | 33 | 131 | 72 |
| Example 25 | 1244 | 57 | 21 | 81 |
| Example 27 | 1976 | 41 | 233 | 75 |
| Example 28 | 1537 | 63 | 238 | 75 |
| Example 29 | 3167 | 18 | 503 | 68 |
| Example 30 | 72 | 88 | 0.1 | 95 |
| Example 31 | 314 | 72 | 2 | 92 |
| Example 32 | 1516 | 26 | 611 | 63 |
| Example 33 | 2933 | 51 | 257 | 75 |
| Example 35 | 10000 | 30 | 727 | 51 |
| Example 37 | 2733 | 27 | 391 | 69 |
| Example 38 | 2562 | 26 | 320 | 63 |
| Example 39 | 260 | 75 | 4 | 87 |
| Example 40 | 836 | 64 | 3 | 95 |
| Example 41 | 10000 | — | 67 | 83 |
| Example 42 | 4197 | 43 | 54 | 88 |
| Example 47 | 10000 | 5 | 3545 | 33 |
| Example 49 | 10000 | 5 | 5478 | 69 |
| Example 50 | 4080 | 25 | 38 | 78 |
| Example 51 | 1893 | 45 | 36 | 88 |
| Example 53 | 2312 | 20 | 266 | 86 |
| Example 60 | 10000 | — | 36 | 81 |
| Example 61 | 2184 | 49 | 26 | 68 |
| Example 62 | 10000 | — | 329 | 54 |
| Example 64 | 10000 | 30 | 303 | 66 |

3. Efficacy

The efficacy of 5-HT$_{2C}$ agonists was assessed for ability to induce a specific syndrome.

The 5-HT$_{2C}$ syndrome is a rapid screening method to assess the in vivo efficacy of 5-HT$_{2C}$ agonists through their ability to induce three specific behaviours in rats. The animals are dosed with either a positive control (mCPP), test compound or vehicle, either sub-cutaneously or p.o. The animals are observed on an open bench, typically 30, 60 and 180 minutes and the degree of syndrome is assessed over a two minute period on a scale of 0–3 depending on the presence and severity of splayed limbs, hunched posture and retro-pulsion, the three specific behaviours which constitute the syndrome. Data is analysed using Kruskal-Wallis Analysis of Variance followed with appropriate post-hoc tests. All statistical analysis are conducted using Excel version 7.0 (Microsoft Corp.) and Statistica version 5.0 (Statsoft, Inc.).

The thus determined activity of Example 1 indicates that after a dose of 30 mg/kg s.c. the compound maintains significant pharmacological efficacy for at least 180 minutes.

SYNTHETIC EXAMPLES

General Method A

Example 1

(RS)-1-(6-Chloroindolin-1-yl)-2-propylamine Hydrochloride

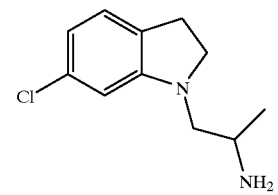

Step (a): (RS)-1-(6-Chloroindol-1-yl)-2-propanol (1a)

To a stirred suspension of sodium hydride (60%, 1.26 g, 31.6 mmol) in tetrahydrofuran (30 mL) at 0° C. under Ar was added dropwise a solution of 6-chloroindole (4.0 g, 26 mmol) in tetrahydrofuran (30 mL). The mixture was stirred for 1 h and (RS)-propylene oxide (3.7 mL, 53 mmol) was added. The mixture was warmed to room temperature, stirred for 48 h and partitioned between aqueous ammonium chloride solution (100 mL) and ether (3×100 mL). The combined organic extracts were washed with brine (2×100 mL), dried (magnesium sulfate), concentrated in vacuo and purified by column chromatography [$SiO_2$; ethyl acetate-hexane (1:9)] to give the product (2.78 g, 50% yield) as a pale yellow oil. Data for the compounds produced using General Method A, step (a) are listed in Table 3.

Step (b): (RS)-1-(2-Azidopropyl)-6-chloroindole (1b)

To a stirred solution of (RS)-1-(6-chloroindol-1-yl)-2-propanol (2.5 g, 11.9 mmol), dichloromethane (60 mL) and triethylamine (1.8 mL, 13 mmol) at 0° C. was added dropwise methanesulfonyl chloride (1 mL, 13 mmol). The mixture was warmed to room temperature, stirred for 1 h and partitioned between brine (50 mL) and dichloromethane (3×50 mL). The combined organic extracts were washed with brine (50 mL), dried (magnesium sulfate) and concentrated in vacuo to give a pale yellow solid (3.3 g), which was added to a stirred mixture of dimethyl formamide (30 mL) and sodium azide (1.1 g, 17 mmol). The mixture was heated to 70° C., stirred for 16 h, cooled to room temperature and partitioned between brine (50 mL) and ether (3×50 mL). The combined organic extracts were washed with brine (50 mL), dried (magnesium sulfate), concentrated in vacuo and purified by column chromatography [$SiO_2$; ether-hexane (1:9)] to give the product (1.7 g, 63% yield) as a colourless oil. Data for (1b) are included in Table 4 with the data for other compounds produced using General Method A, step (b).

Step (c): (RS)-1-(2-Azidopropyl)-6-chloroindoline (1c)

To a stirred solution of (RS)-1-(2-azidopropyl)-6-chloroindole (1.5 g, 6.4 mmol) in acetic acid (25 mL) at 5° C. was added portionwise sodium cyanoborohydride (1.2 g, 19 mmol). The mixture was warmed to room temperature, stirred for 16 h and partitioned between ether (100 mL) and aqueous sodium bicarbonate solution (4×100 mL). The organic layer was washed (brine), dried (magnesium sulfate), concentrated in vacuo and purified by column chromatography [$SiO_2$:ethyl acetate-hexane (1:9)] to give the product (1.39 g, 92% yield) as a pale yellow oil. Data for (1c) are included in Table 5 with the data for other compounds produced using General Method A, step (c).

Step (d): (RS)-1-(6-Chloroindolin-1-yl)-2-propylamine Hydrochloride (1)

To a stirred solution of (RS)-1-(2-azidopropyl)-6-chloroindoline (0.92 g, 1.8 mmol) in tetrahydrofuran (70 mL) at 0° C. under Ar was added portionwise a mixture of Zinc powder (1.3 g, 20 mmol) and nickel chloride hexahydrate (6.8 g, 28 mmol). The mixture was warmed to room temperature, stirred for 16 h, and partitioned between water (50 mL) and ethyl acetate (3×30 mL). The combined organic extracts were washed (brine), dried (magnesium sulfate) and concentrated in vacuo to give a pale brown oil. The oil was dissolved in a mixture of ether (10 mL) and dichloromethane (20 mL) and the solution was cooled to 0° C. Ethereal hydrogen chloride solution (1.0 M, 3.9 mL, 3.9 mmol) was added dropwise and the mixture stirred at room temperature for 10 min. The mixture was concentrated in vacuo and recrystallised (2-propanol) to give the product (0.42 g, 38% yield) as a pale pink solid. Data for (1) are included in Table 6 with the data for other compounds produced using General Method A, step (d).

Alternative Step (d): (RS)-1-(6-Methoxyindolin-1-yl)-2-propylamine Hydrochloride (2)

A mixture of (RS)-1-(2-azidopropyl)-6-methoxyindoline (0.27 g, 1.1 mmol), ethanol (10 mL) and platinum(IV)oxide (0.01 g, 0.04 mmol) was stirred under hydrogen for 12 h. The mixture was filtered through a pad of Celite® and concentrated in vacuo to give a pale yellow oil, which was dissolved in ether (5 mL) and cooled to 0° C. Ethereal hydrogen chloride solution (1.0 M, 1.1 mL, 1.1 mmol) was added dropwise and the mixture was was concentrated in vacuo and recrystallised (2-propanol) to give the product (0.18 g, 64%) as a pale blue solid. Data for (2) are included in Table 6 with the data for other compounds produced using General Method A, step (d).

The compounds shown in Tables 3, 4, 5 and 6 were prepared using General Method A from (RS)-propylene oxide, (R)-propylene oxide, (RS)-1,2-epoxybutane and fumaric acid as appropriate.

TABLE 3

Indoles prepared using General Method A, step(a)

| No | | Data |
|---|---|---|
| 1a | R = 6-Cl<br>R' = Me | IR $v_{max}$ (film)/cm$^{-1}$ 3387, 2972, 2931, 1711, 1608, 1506, 1465, 1396, 1377, 1339, 1320, 1243, 1200, 1139, 1091, 1065, 938, 908, 898, 839, 805, 721, 673, 605 and 492; NMR $\delta_H$ (400 MHz, CDCl$_3$) 1.26(3H, d, J 6Hz), 3.98(1H, dd, J 8, 14.5Hz), 4.12(1H, dd, J 3.5, 14.5Hz), 4.19(2H, m), 6.49(1H, d, J 3.5Hz), 7.07(1H, dd, J, 2, 8.5Hz), 7.13(1H, d, J 3.5Hz), 7.36(1H, d, J 2Hz), 7.52(1H, d, J 8.5Hz). |
| 2a | R = 6-OMe<br>R' = Me | NMR $\delta_H$ (400 MHz, CDCl$_3$) 1.26(3H, d, J 6Hz), 3.86(3H, s), 3.96(1H, dd, J 14 and 8Hz), 4.08(1H, dd, J 14 and 4 Hz), 4.15(1H, m), 6.43(1H, d, J 3Hz), 6.82(2H, m), 7.01 (1H, d, J 3Hz), 8.5(1H, d, J 8.5Hz). |
| 3a | R = 6-Me<br>R' = Me | IR $v_{max}$ (film)/cm$^{-1}$ 3406, 1621, 1510, 1469, 937, 802 and 718; NMR $\delta_H$ (400 MHz, CDCl$_3$) 1.25(3H, d, J 6Hz), 2.47 |

TABLE 3-continued

Indoles prepared using General Method A, step(a)

| No | | Data |
|---|---|---|
| | | (3H, s), 3.99(1H, m), 4.19(2H, m), 6.45(1H, d, J 2.5Hz), 6.95(1H, d, J 8Hz), 7.04(1H, d, J 2.5Hz), 7.14(1H, m) and 7.50(1H, d, J 8Hz) |
| 4a | R = 5-OBn<br>R' = Me | mp 72° C. Found: C, 76.81; H, 6.79; N, 5.00%. $C_{18}H_{19}NO_2$ requires: C, 76.84; H, 6.81; N, 4.98%. |
| 5a | R = 4-OBn<br>R' = Me | IR $\nu_{max}$ (film)/cm$^{-1}$ 3412, 1578, 1496, 1453, 1368, 1255, 1056 and 736; NMR $\delta_H$ (400 MHz, CDCl$_3$), 1.23(3H, d, J 6.5Hz), 1.78(1H, br s), 3.91–3.99(1H, m), 4.04–4.18(2H, m), 5.23(2H, s), 6.59,(1H, d, J 8Hz), 6.70(1H, d, J 4Hz), 6.99,(1H, d, J, 8.5Hz), 7.05(1H, d, J 3.5Hz), 7.12,(1H, t, J 7.5Hz), 7.28–7.34(1H, m), 7.35–7.47(2H, m) and 7.46–7.52(2H, m). |
| 6a | R = 6-Cl<br>R' = Et | IR $\nu_{max}$ (film)/cm$^{-1}$ 3396, 2967, 1608, 1464, 1319, 901 and 720; NMR $\delta_H$ (400 MHz, CDCl$_3$) 1.05(3H, t, J 7.5Hz), 1.37–1.60(2H, m), 1.82–1.88(1H, brs), 3.76–3.85(1H, m), 3.87–3.97(1H, m), 4.15(1H, dd, J 14.5, 3.5Hz), 6.41–6.48 (1H, m), 7.02–7.13(2H, m), 7.31–7.35(1H, m) and 7.46–7.53(1H, m) |
| 7a | R = 6-OBn<br>R' = Me | IR $\nu_{max}$ (film)/cm$^{-1}$ 3419, 1622, 1488, 1466, 1454, 1377, 1316, 1262, 1191, 1095, 1025 and 809;(400 MHz, CDCl$_3$), 1.23(3H, d, J 6.5), 3.9–3.98(1H, m), 4.03–4.19(2H, m), 5.12(2H, s), 6.42–6.46(1H, m), 6.85–6.92(2H, m), 7.02 (1H, d, J 3Hz), 7.29–7.35(1H, m), 7.36–7.42(2H, m) and 7.44–7.52(3H, m) |
| 8a | R = 6-CF$_3$<br>R' = Me | IR $\nu_{max}$ (film)/cm$^{-1}$ 3353, 3285, 1468, 1354, 1311, 1250, 1154, 1092, 1054 and 813; NMR $\delta_H$ (400 MHz, CDCl$_3$) 1.25(3H, d, J 6.5Hz), 4.01–4.08(1H, m), 4.13–4.22(1H, m), 6.55(1H, d, J 3Hz), 7.27(1H, d, J 3Hz), 7.34(1H, d, J 8Hz), 7.63(1H, s) and 7.68(1H, d, J 8Hz) |
| 9a | R = 6-F<br>R' = Me(R) | IR $\nu_{max}$ (film)/cm$^{-1}$ 3384, 1621, 1488, 949 and 718; NMR $\delta_H$ (400 MHz, CDCl$_3$) 1.17(3H, d, J 6Hz), 3.88(1H, dd, J 7.5Hz), 4.04–4.06(1H, m), 4.06–4.09(1H, m), 6.43(1H, d, J 3Hz), 6.82–6.87(1H, m), 7.01(1H, dd, J 9.5, 2.5Hz), 7.05(1H, d, J 3Hz) and 7.49(1H, dd, J 8.5, 5Hz) |

TABLE 4

Indoles prepared using General Method A, step(b)

| No | | Data |
|---|---|---|
| 1b | R = 6-Cl<br>R' = Me | IR $\nu_{max}$ (film)/cm$^{-1}$ 2934, 2117, 1607, 1464, 806, 720 and 603; NMR $\delta_H$ (400 MHz, CDCl$_3$) 1.29(3H, d, J 6.5Hz), 3.90(1H, m), 4.05(2H, m), 6.52(1H, m), 7.10(2H, m), 7.31(1H, m) and 7.53(1H, d, J 8Hz) |
| 2b | R = 6-OMe<br>R' = Me | NMR $\delta_H$ (400 MHz, CDCl$_3$) 1.26(3H, d, J 6Hz), 3.86(3H, s), 3.96(1H, dd, J 14 and 8Hz), 4.08(1H, dd, J 14 and 4 Hz), 4.15(1H, m), 6.43(1H, d, J 3Hz), 6.82(2H, m), 7.01 (1H, d, J 3Hz), 8.5(1H, d, J 8.5Hz) |
| 3b | R = 6-Me<br>R' = Me | IR $\nu_{max}$ (film)/cm$^{-1}$ 2117, 1621, 1467, 1259, 803 and 717; NMR $\delta_H$ (400 MHz, CDCl$_3$) 1.30(3H, d, J 6.5Hz), 2.50 (3H, s), 3.96(1H, m), 4.09(2H, m), 6.49(1H, d, J 3Hz), 6.97(1H, d, J 8Hz), 7.04(1H, d, J 3Hz), 7.11(1H, s) and 7.53(1H, d, J 8Hz). |
| 4b | R = 5-OBn<br>R' = Me | IR $\nu_{max}$ (film)/cm$^{-1}$ 2975, 2932, 2870, 2118, 1726, 1621, 1576, 1485, 1453, 1382, 1258, 1238, 1154, 1025, 847, 790, 720, 624 and 554; NMR $\delta_H$ (400 MHz, CDCl$_3$) 1.25(3H, d, |

TABLE 4-continued

Indoles prepared using General Method A, step(b)

| No | | Data |
|---|---|---|
| | | J 6.5Hz) 3.88(1H, m) 4.05(2H, m) 5.08(2H, s) 6.43(1H, d, J 4Hz) 6.95(1H, dd, J 2.5, 8.5Hz) 7.06(1H, d, J 3Hz) 7.16(1H, d, J 2.5Hz) 7.22(1H, m) 7.30(1H, t, J 7Hz) 7.37 (2H, t, J 7Hz) 7.46(2H, d, J 7Hz). |
| 5b | R = 4-OBn<br>R' = Me | IR $\nu_{max}$ (film)/cm$^{-1}$ 2117, 1579, 1496, 1453, 1369, 1256, 1056 and 736; NMR $\delta_H$ (400 MHz, CDCl$_3$), 1.26(3H, d, J 6.5Hz), 3.91(1H, m), 4.07(2H, d, J 6Hz), 5.22(2H, s), 6.59(1H, d, J 7.5Hz), 6.7(1H, d, J 4Hz), 6.95(1H, d, J 8 Hz), 7.01,(1H, d, J 3Hz), 7.12(1H, t, J 7.5Hz), 7.29–7.34 (1H, m), 7.36–7.42(2H, m) and 7.47–7.53(2H, m) |
| 6b | R = 6-Cl<br>R' = Et | IR $\nu_{max}$ (film)/cm$^{-1}$ 2970, 2935, 2099, 1464, 901, 806 and 719; NMR $\delta_H$ (400 MHz, CDCl$_3$) 1.10(3H, t, J 7.5Hz), 1.42–1.71(2H, m), 3.56–3.68(1H, m), 3.90–4.0(1H, m), 4.07–4.16(1H, m), 6.45–6.54(1H, m), 7.03–7.12(2H, m), 7.28–7.31(1H, m) and 7.48–7.56(1H, m) |
| 7b | R = 6-OBn<br>R' = Me | IR $\nu_{max}$ (film)/cm$^{-1}$ 2117, 1622, 1488, 1264, 1194, 1025 and 809;(400 MHz, CDCl$_3$), 1.24(3H, d, J 6.5Hz), 3.85(1H, m), 4.01(2H, d, J 6.5Hz), 5.13(2H, s), 6.44–6.47(1H, m), 6.82–6.91(2H, m), 6.99(1H, d, 3Hz), 7.29–7.35(1H, m) and 7.45-7.53(3H, m) |
| 8b | R = 6-CF$_3$<br>R' = Me | IR $\nu_{max}$ (film)/cm$^{-1}$ 2117, 1617, 1455, 1318 and 1118; NMR $\delta_H$ (400 MHz, CDCl$_3$)1.31(3H, d, J 7.5Hz), 3.01–3.07(2H, m), 3.10–3.15(2H, m), 3.49–3.59(2H, m), 3.74–3.78(1H, m), 6.58(1H, s), 6.90–6.92(2H, m) and 7.10–7.12(1H, m) |
| 9b | R = 6-F<br>R' = Me, (S) | IR $\nu_{max}$ (film)/cm$^{-1}$ 2119, 1621, 1468, 1255, 948 and 717; NMR $\delta_H$ (400 MHz, CDCl$_3$) 1.25(3H, d, J 6Hz), 3.87–4.03 (3H, m), 6.48(1H, d, J 3Hz), 6.82–6.86(1H, m), 6.98(1H, dd, J 9.5, 2.5Hz), 7.05(1H, d, J 3Hz) and 7.51(1H, dd, J 8.5, 5.5Hz) |

TABLE 5

Indolines prepared using General Method A, step(c)

| No | | Data |
|---|---|---|
| 1c | R = 6-Cl<br>R' = Me | IR $\nu_{max}$ (film)/cm$^{-1}$ 2642, 2115, 1606, 1493, 1271, 1010, 879 and 589; NMR $\delta_H$ (400 MHz, CDCl$_3$) 1.30(3H, d, J 6.5 Hz), 2.96(2H, m), 3.07(2H, m), 3.52(2H, m), 3.76(1H, m), 6.39(1H, d, J 2Hz), 6.60(1H, dd, J 7.5 and 2Hz) and 6.94(1H, d, J 7.5Hz). |
| 2c | R = 6-OMe<br>R' = Me | IR $\nu_{max}$ (film)/cm$^{-1}$ 2115, 1621, 1498, 1211, 820 and 631; NMR $\delta_H$ (400 MHz, CDCl$_3$) 1.29(3H, d, J 6.5Hz), 2.93 (2H, m), 3.16(2H, m), 3.46(2H, m), 3.76(1H, m), 6.04 (1H, d, J 2Hz), 6.18(1H, dd, J 8 and 2Hz) and 6.95(1H, d, J 8Hz) |
| 3c | R = 6-Me<br>R' = Me | IR $\nu_{max}$ (film)/cm$^{-1}$ 2115, 1614, 1647, 1020 and 796; NMR $\delta_H$ (400 MHz, CDCl$_3$) 1.32(3H, d, J 6.5Hz), 2.29(3H, s), 2.98(2H, m), 3.06(1H, m), 3.16(1H, m), 3.50(2H, m), 3.78(1H, m), 6.29(1H, m), 6.50(1H, d, J 7Hz) and 6.97 (1H, d, J 7Hz). |
| 5c | R = 4-OBn<br>R' = Me | IR $\nu_{max}$ (film)/cm$^{-1}$ 2114, 1615, 1464, 1228, 1062 and 754; NMR $\delta_H$ (400 MHz, CDCl$_3$) 1.29,(3H, d, J 6.5Hz), 2.98–3.09(3H, m), 3.11–3.18(1H, m), 3.42–3.56(2H, m), 3.75 (1H, m), 5.08(2H, s), 6.16(1H, d, J 8Hz), 6.33(1H, d, J 8 Hz), 6.97–7.06(1H, m), 7.28–7.33(1H, m) and 7.34–7.44 (4H, m) |

TABLE 5-continued

Indolines prepared using General Method A, step(c)

| No | | Data |
|---|---|---|
| 6c | R = 6-Cl<br>R' = Et | IR $v_{max}$ (film)/cm$^{-1}$ 2968, 2934, 2097, 1606, 1493, 1271 and 883; NMR $\delta_H$ (400 MHz, CDCl$_3$) 1.07(3H, t, J 7.5Hz), 1.48–1.66(2H, m), 2.93–2.97(2H, m), 3.07–3.14(2H, m), 3.46–3.56(3H, m), 6.36–6.40(1H, m), 6.55–6.63(1H, m) and 6.89–6.99(1H, m) |
| 7c | R = 6-OBn<br>R' = Me | IR $v_{max}$ (film)/cm$^{-1}$ 2115, 1620, 1498, 1285, 1191, 1091, 1025 and 735;(400 MHz, CDCl$_3$), 1.27(3H, d, J 6.5Hz), 2.94(2H, t, J 8Hz), 3.06(2H, m), 3.48(2H, m), 3.74(1H, m), 5.02(2H, s), 6.12(1H, d, J 2Hz), 6.23–6.28(1H, m), 6.91–6.97(1H, d, 8Hz) and 7.27–7.46(5H, m) |
| 8c | R = 6-CF$_3$<br>R' = Me | IR $v_{max}$ (film)/cm$^{-1}$ 3373, 2976, 2935, 2847, 2117, 1617, 1318 and 663; NMR $\delta_H$ (400 MHz, CDCl$_3$) 1.18(3H, d, J 7 Hz) 2.93–3.20(4H, m) 3.45–3.55(2H, m) 3.71–3.75(1H, m) 6.34–6.44(1H, m) 6.80–6.85(1H, m) and 7.10–7.20(1H, m) |
| 9c | R = 6-F<br>R' = Me, (S) | IR $v_{max}$ (film)/cm$^{-1}$ 2116, 1619, 1496, 1275, 822 and 612; NMR $\delta_H$ (400 MHz, CDCl$_3$) 1.28(3H, d, J 6.5Hz) 2.93–2.95(2H, m), 3.04–3.06(2H, m), 3.51–3.53(2H, m), 3.72–3.74(1H, m), 6.13(1H, dd, J 10, 2.5Hz), 6.29-6.31(1H, m) and 6.93–6.95(1H, m) |

TABLE 6

Examples 1–9. Indolines prepared using General Method A, step(d)

| No | Structure | Data |
|---|---|---|
| 1 | (6-Cl indoline with CH$_2$CH(CH$_3$)NH$_2$) | HCl. mp 262° C.; IR $v_{max}$ (Nujol)/cm$^{-1}$ 2924, 1589, 1489, 1462, 882 and 840; NMR $\delta_H$ (400 Mz, DMSO-d$_6$) 1.28(3H, d, J 6.5Hz), 2.54(2H, m), 2.94(2H, m), 3.08(1H, m), 3.34(2H, m), 3.46(1H, m), 3.58(1H, m), 6.64(2H, m), 7.64(1H, d, J 7.5Hz) and 8.0(3H, br). |
| 2 | (6-OMe indoline with CH$_2$CH(CH$_3$)NH$_2$) | HCl. mp 142–143° C.; IR $v_{max}$ (Nujol)/cm$^{-1}$ 2924, 1619, 1496, 1464, 1098, 831 and 788; NMR $\delta_H$ (400 MHz, DMSO-d$_6$) 1.25(3H, d, J 6.5Hz), 2.50(3H, s), 3.02(1H, m), 3.08(2H, m), 3.26(2H, m), 3.40(1H, m), 3.49(2H, m), 6.24(1H, m), 6.24(1H, m), 6.92(1H, d, J 8Hz) and 8.05(3H, br). |
| 3 | (6-Me indoline with CH$_2$CH(CH$_3$)NH$_2$) | HCl. mp 178–179° C., IR $v_{max}$ (Nujol)/cm$^{-1}$ 3345, 2925, 1613, 1494, 1460, 1270, 1186 and 796; NMR $\delta_H$ (400 MHz, DMSO-d$_6$) 1.25(3H, d, J 6.5Hz), 2.19(3H, s), 2.87(2H, m), 2.99(1H, dd, J 14 and 5Hz), 3.22(2H, m), 3.43(2H, m), 6.43(2H, m), 6.92(1H, d, J 8Hz) and 8.05(3H, br). |

TABLE 6-continued

Examples 1–9. Indolines prepared using General Method A, step(d)

| No | Structure | Data |
|---|---|---|
| 4 | 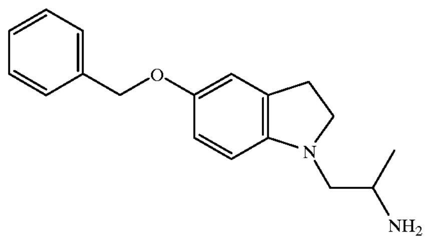 | Fumarate mp 143–4° C.; Found: C, 65.69; H, 6.53; N, 6.95% $C_{18}H_{22}N_2O \cdot C_4H_4O_4 \cdot 0.25\ H_2O$ requires C, 65.57; H, 6.63; N, 6.95%. |
| 5 | 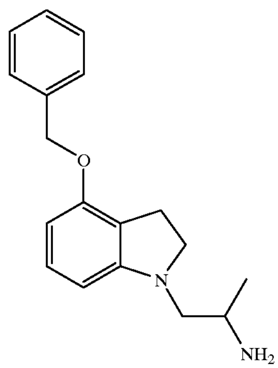 | HCl. mp 188–190° C.; Found: C, 67.79; H, 7.35; N, 8.70%. $C_{18}H_{22}N_2O \cdot HCl$ requires: C, 67.81; H, 7.27; N, 8.78%; IR $v_{max}$ (Nujol)/cm$^{-1}$ 1614, 1460, 1377, 1257, 1237, 1064 and 758; NMR $\delta_H$ (400 MHz, DMSO-d$_6$), 1.26(3H, d, 16.5Hz), 2.79–2.96(2H, m), 2.97–3.05(1H, m), 3.23–3.34(2H, m), 3.35–3.43(1H, m), 3.45–3.54(2H, m), 5.09(2H, m), 6.29 (1H, d, J 7.5Hz), 6.39(1H, d, J 7.5Hz), 7.28–7.34(1H, m), 7.39–7.44(4H, m) and 8.22(3H, br s). |
| 6 | 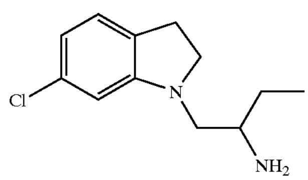 | HCl. mp 188–192° C.; NMR $\delta_H$ (400 MHz, DMSO-d$_6$) 0.75(3H, t, J 7.5Hz), 1.27–1.44(2H, m), 2.57–2.68(1H, m), 2.77–2.89(1H, m), 2.88–3.12(4H, m), 3.23–3.34(1H, m), 6.30–6.38(2H, m) and 6.71–6.80(1H, m). |
| 7 | 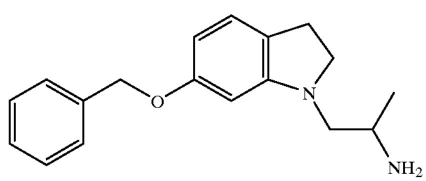 | mp 178–179° C.;, Found: C, 70.21; H, 7.12; N, 8.00%. $C_{18}H_{22}N_2O \cdot 0.5\ C_4H_4O_4$ requires: C, 75.56; H, 7.11; N, 8.23%; IR $v_{max}$ (Nujol)/cm$^{-1}$ 1621, 1545, 1456, 1349, 1181, 1024, 732 and 667; ;(400 MHz, d$_6$DMSO), 1.15(3H, d, J 6.5Hz), 2.78–2.87(2H, m), 2.89–2.99(1H, m), 3.09–3.17 (1H, m), 3.22–3.32(2H, m), 3.4–3.48(1H, m), 5.01(2H, s), 6.2(1H, d, J 6.5), 6.24(1H, m), 6.39(1H, s), 6.89(1H, d, J 8Hz) and 7.27–7.45(5H, m) |
| 8 | 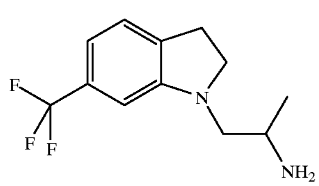 | Fumarate. mp 154–8° C.; IR $v_{max}$ (Nujol)/cm$^{-1}$ 1618, 1457, 1378, 1318, 1162, 1118 and 1060. |
| 9 | Chiral | Fumarate. mp 150–153° C.; NMR $\delta_H$ (400 MHz, DMSO-d$_6$) 1.20(3H, d, J 6.0Hz), 2.86–2.88(1H, m), 3.01(1H, dd, J 14, 5.5Hz), 3.23–3.25(1H, m), 3.34–3.36(2H, m), 3.52–3.56 (1H, m), 6.30–6.32(1H, m), 6.40–6.45(1H, m) and 6.97–6.99(1H, m). |

General Method B

Example 10
(S)-1-(6-Chloroindolin-1-yl)-2-propylamine Fumarate

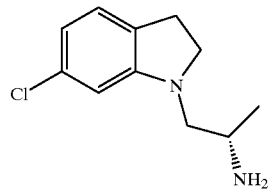

Step (a): (S)-1-[2-(tert-Butoxycarbonylamino)propyl]-6-chloroindole (10a)

6-Chloroindole (1.5 g, 10 mmol) was added portionwise to a stirred suspension of powdered potassium hydroxide (2.24 g, 40 mmol) in methyl sulfoxide (25 mL). The mixture was warmed to 35° C. and stirred for 30 min. A solution of (S)-2-(tert-butoxycarbonylamino)propane methanesulfonate (6.3 g, 25 mmol) in methyl sulfoxide (10 mL) was added over 2 h. The mixture was stirred for 20 h and partitioned between water (50 mL) and ether (3×30 mL). The combined organic extracts were washed with brine (2×), dried (magnesium sulfate), concentrated in vacuo and purified by column chromatography [SiO$_2$; heptane-ethyl acetate (6:1)] to give the product (0.75 g, 24% yield) as a pink solid. Data for (10a) are included in Table 7 with the data for other compounds produced using General Method B, step (a).

Step (b): (S)-1-[2-(tert-Butoxycarbonylamino)propyl]-6-chloroindoline (10b)

To a stirred solution of (S)-1-[2-(tert-butoxycarbonylamino)propyl]-6-chloroindole (0.7 g, 2.3 mmol) in acetic acid (15 mL) was added portionwise sodium cyanoborohydride (0.43 g, 6.9 mmol). The mixture was stirred for 16 h and partitioned between ether (40 mL) and saturated aqueous sodium bicarbonate solution (3×50 mL). The organic layer was washed with brine (2×), dried (magnesium sulfate), concentrated in vacuo and purified by column chromatography [SiO$_2$; heptane-ethyl acetate (6:1)] to give the product (0.57 g, 80%) as a white solid. Data for (10b) are included in Table 8 with the data for other compounds produced using General Method B, step (b).

Step (c): (S)-1-(6-Chloroindolin-1-yl)-2-propylamine Fumarate (10)

To a stirred solution of (S)-1-[2-(tert-butoxycarbonylamino)propyl]-6-chloroindoline (0.5 g, 1.6 mmol) in dichloromethane (5 mL) was added dropwise trifluoroacetic acid (5 mL). The mixture was stirred for 1 h and partitioned between aqueous sodium hydroxide solution (2 M, 50 mL) and dichloromethane (3×30 mL). The combined organic extracts were washed with brine (2×), dried (magnesium sulfate) and concentrated in vacuo to give a pale yellow oil. The oil was dissolved in 2-propanol (5 mL) and the solution was heated to boiling then fumaric acid (0.18 g, 1.6 mmol) was added. The mixture was cooled to room temperature and filtered. The filter-cake was dried in vacuo to give the product (0.39 g, 75%) as a white solid. Data for (10) is included in Table 9 with the data for other compounds produced using General Method B, step (c).

The compounds shown in Tables 7, 8 and 9 were prepared using General Method B from either commercially available indoles or from indoles synthesised according to the methods described after Table 9 using (RS)-2-(tert-butoxycarbonylamino)propane methanesulfonate, (S)-2-(tert-butoxycarbonylamino)propane methanesulfonate or (R)-2-(tert-butoxycarbonylamino)propane methanesulfonate as appropriate.

TABLE 7

Indoles prepared using General Method B, step (a)

| No | R | Data |
|---|---|---|
| 10a | 6-Cl (S) | mp 144–146° C.; NMR δ$_H$ (400 MHz, CDCl$_3$) 1.14(3H, d, J 6.5 Hz), 1.45(9H, s), 4.02–4.49(4H, m), 6.51(1H, d, J 3 Hz), 7.06–7.12(2H, m), 7.42(1H, brs) and 7.54(1H, d, J 9 Hz). |
| 11a | 7-OBn (RS) | IR ν$_{max}$ (Nujol)/cm$^{-1}$ 3366, 1684, 1526, 1455, 1373, 1319, 1175, 1058 and 717; NMR δ$_H$ (400 MHz, CDCl$_3$) 0.871 (3H, br s), 0.93–1.36(9H, m), 3.84–4.01(1H, m), 4.21–4.44 (2H, m), 4.69–4.84(1H, m), 5.18(2H, br s), 6.43(1H, br s), 6.72(1H, d, J 7.5 Hz), 7.22(1H, d, J 7.5 Hz) and 7.34–7.53 (5H, m). |
| 12a | 6-Br (S) | IR ν$_{max}$ (neat)/cm$^{-1}$ 2941, 1739, 1574, 1498, 1270, 1033 and 828; NMR δ$_H$ (400 MHz, CDCl$_3$) 1.12(3H, d, J 7 Hz), 1.43(9H, s), 3.68–3.74(1H, m), 4.0–4.18(2H, m), 4.42(1H, brs), 6.48(1H, d, J 3 Hz), 7.04(d, J 3 hz), 7.19(1H, dd, J 8.5, 1 Hz), 7.46(d, J 8.5 Hz) and 7.54(1H, brs). |
| 13a | 6-OMe (S) | IR ν$_{max}$ (Nujol)/cm$^{-1}$ 1683, 1458, 1363, 1220, 1051, 812 and 625; NMR δ$_H$ (400 MHz, CDCl$_3$) 1.17(3H, d, J 7 Hz), 1.50(9H, s), 3.93(3H, s), 3.98–4.10(3H, m), 4.52(1H, brs), 6.41–6.45(1H, m), 6.74–6.83(1H, m), 6.94–6.99(1H, m), and 7.46–7.53(1H, m). |
| 14a | 5-Me, 6-Cl (S) | IR ν$_{max}$ (Nujol)/cm$^{-1}$ 1681, 1531, 1463, 1165, 1061, 974 and 645; NMR δ$_H$ (400 MHz, CDCl$_3$) 1.01(3H, d, J 6 Hz), 1.44(9H, s), 2.43(3H, s), 4.01–4.16(3H, m), 4.38(1H, brs), 6.41(1H, d, J 3 Hz), 7.01(1H, d, J 3 Hz), 7.40(1H, s) and 7.44(1H, s). |

TABLE 7-continued

Indoles prepared using General Method B, step (a)

| No | R | Data |
|---|---|---|
| 15a | 5-F, 6-Cl (R) | IR ν$_{max}$ (Nujol)/cm$^{-1}$ 1680, 1532, 1461, 1168, 815 and 715; NMR δ$_H$ (400 MHz, CDCl$_3$) 1.1(3H, d, J 8 Hz), 1.42(9H, s), 4.01–4.13(3H, m), 4.36(1H, brs), 6.43(d, J 3 Hz), 7.07 (1H, d J 3 Hz), 7.30(1H, d, J 6 Hz) and 7.40(1H, d, J 6 Hz). |
| 16a | 5-F, 6-Cl (S) | IR ν$_{max}$ (film)/cm$^{-1}$ 1680, 1531, 1370, 1064 and 815; NMR δ$_H$ (400 MHz, CDCl$_3$) 1.1(3H, d, J 8 Hz), 1.42(9H, s), 4.01–4.13(3H, m), 4.36(1H, brs), 6.43(d, J 3 Hz), 7.07 (1H, d, J 3 Hz), 7.30(1H, d, J 6 Hz) and 7.40(1H, d, J 6 Hz). |
| 17a | 5-F, 7-Cl (S) | IR ν$_{max}$ (Nujol)/cm$^{-1}$ 1683, 1528, 1459, 1060 and 717; NMR δ$_H$ (400 MHz, CDCl$_3$) 1.15(3H, d, J 6 Hz), 1.28(9H, s), 3.97–4.07(1H, m), 4.35–4.56(3H, m), 6.44(1H, d, J 3 Hz), 6.94(1H, dd, J 9, 2.5 Hz), 7.07(1H, brs) and 7.14 (1H, dd, J 9, 2.5 Hz). |
| 18a | 6-Br (R) | IR ν$_{max}$ (Nujol)/cm$^{-1}$ 1683, 1533, 1462, 1173, 1062, 799 and 718; NMR δ$_H$ (400 MHz, CDCl$_3$) 1.12(3H, d, J 7 Hz), 1.43(9H, s), 4.0–4.15(3H, m), 4.39(1H, brs), 6.48(1H, d, J 3 Hz), 7.04(1H, d, J 3 Hz), 7.20(1H, dd, J 8.5, 2 Hz), 7.46 (1H, d, J 8.5 Hz) and 7.54(1H, brs). |
| 19a | 7-Br (R) | IR ν$_{max}$ (Nujol)/cm$^{-1}$ 1682, 1528, 1453, 1316, 1173, 777 and 713; NMR δ$_H$ (400 MHz, CDCl$_3$) 1.22(3H, d, J 7 Hz), 1.29(9H, s), 4.40–4.48(1H, m), 4.50–4.69(3H, m), 6.52 (1H, d, J 3 Hz), 6.95(1H, t, J 8 Hz), 7.11(1H, brs), 7.36–7.39(1H, m) and 7.56–7.58(1H, m). |
| 20a | 7-Br (S) | IR ν$_{max}$ (Nujol)/cm$^{-1}$ 1683, 1528, 1453, 1316, 1173, 1059, 777 and 713; NMR δ$_H$ (400 MHz, CDCl$_3$) 1.17(3H, d, J 7 Hz), 1.28(9H, s), 3.94–4.71(4H, m), 6.47(1H, d, J 3 Hz), 6.89(1H, t, J 7 Hz), 7.06(1H, brs), 7.32(1H, dd J 7.5, 1 Hz) and 7.52(1H, dd, J 8, 1 Hz). |
| 21a | 6,7-dichloro (R) | IR ν$_{max}$ (Nujol)/cm$^{-1}$ 1684, 1526, 1458, 1317, 1061, 800 and 720; NMR δ$_H$ (400 MHz, CDCl$_3$) 1.24(3H, d, J 6.5 Hz), 1.34(9H, s), 4.43–4.51(1H, m), 4.58–4.65(4H, m), 6.50(1H, d, J 3 Hz), 7.09(1H, brs), 7.19(1H, d, J 8.5 Hz) and 7.44(1H, d, J 8.5 Hz). |
| 23a | 6,7-dichloro (S) | IR ν$_{max}$ (Nujol)/cm$^{-1}$ 1685, 1526, 1317, 1179, 1061, 800 and 719; NMR δ$_H$ (400 MHz, CDCl$_3$) 1.16(3H, d, J 7 Hz), 1.89(9H, s), 3.92–4.11(2H, m), 4.35–4.56(1H, m), 4.58 (1H, brs), 6.45(1H, d, J 3 hz), 7.04(1H, brs), 7.14(1H, d, J 8.5 Hz) and 7.38(1H, d, J 8.5 Hz). |
| 24a | 6-CF$_3$ (S) | IR ν$_{max}$ (Nujol)/cm$^{-1}$ 1684, 1533, 1348, 1109, 812 and 622; NMR δ$_H$ (400 MHz, CDCl$_3$) 1.09(3H, d, J 6.5 Hz), 1.33 (9H, s), 3.99-4.19(3H, m), 4.39(1H, brs), 6.52(1H, d, J 3 Hz), 7.17(1H, d, J 3 Hz), 7.28(1H, d, J 9 Hz) and 7.61–7.64 (1H, m). |
| 25a | 5-F, 6-Br (S) | IR ν$_{max}$ (Nujol)/cm$^{-1}$ 1679, 1533, 1479, 1165, 1064, 812 and 663; NMR δ$_H$ (400 MHz, CDCl$_3$) 1.12(3H, d, J 6.5 Hz), 1.42(9H, s), 3.99–4.08(1H, m), 4.10–4.08(2H, m), 4.39(1H, brs), 6.45(1H, d, J 3 Hz), 7.1(1H, d, J 3 Hz), 7.36(1H, d, J 9 Hz) and 7.56(1H, d, J 5.5 Hz). |
| 26a | 6-CF$_3$ (R) | IR ν$_{max}$ (Nujol)/cm$^{-1}$ 1683, 1533, 1461, 1308, 1109, 812 and 662; NMR δ$_H$ (400 MHz, CDCl$_3$) 1.14(3H, d, J 7.5 Hz), 1.39(9H, s), 4.06–4.12(3H, m), 4.39(1H, brs), 6.58 (1H, d, J 3 Hz), 7.23(1H, d, J 3 Hz), 7.34(1H, d, J 8 Hz) and 7.70(1H, d, J 8 Hz). |
| 27a | 6-Cl, 7-F (S) | IR ν$_{max}$ (Nujol)/cm$^{-1}$ 1687, 1615, 1197, 1080 and 543; NMR δ$_H$ (400 MHz, CDCl$_3$) 1.15(3H, d, J 6.5 hz), 1.31 (9H, s), 3.99–4.08(1H, m), 4.28–4.43(3H, m), 6.46–6.48 (1H, m), 7.01(1H, dd, J 6.5 Hz), 7.04(1H, brs) and 7.24–7.26(1H, m). |
| 28a | 5-Cl (S) | IR ν$_{max}$ (Nujol)/cm$^{-1}$ 1683, 1516, 1174, 1076 and 716; NMR δ$_H$ (400 MHz, CDCl$_3$) 1.15(3H, d, J 6.5 Hz), 1.48 (9H, s), 4.04–4.17(1H, m), 4.26–4.35(2H, m), 4.43(1H, brs), 6.49(1H, d, J 3 Hz), 7.13(1H, d, J 3 Hz), 7.21(1H, dd, J 8, 2 Hz), 7.41(1H, d, J 8 Hz) and 7.63(1H, d, J 2 Hz). |

TABLE 7-continued

Indoles prepared using General Method B, step (a)

| No | R | Data |
|---|---|---|
| 29a | 5-F (S) | IR ν$_{max}$ (Nujol)/cm$^{-1}$ 1684, 1515, 1488, 1364, 1172, 1075 and 718; NMR δ$_H$ (400 MHz, CDCl$_3$) 1.16(3H, d, J 7 Hz), 1.49(9H, s), 4.06–4.16(2H, m), 4.27–4.36(1H, m), 4.45 (1H, brs), 6.51(1H, d, J 3 Hz), 7.0(1H, td, J 8.5, 2.5 Hz), 7.15(1H, d, J 3 Hz), 7.28–7.32(2H, m) and 7.41(1H, brs). |
| 30a | 5-F, 6-MeS (S) | mp 119–124° C.; IR ν$_{max}$ (Nujol)/cm$^{-1}$ 3361, 2924, 2854, 1678, 1531, 1475, 1164 and 1064; NMR δ$_H$ (400 MHz, CDCl$_3$) 1.12(3H, d, J 6.0 Hz), 1.43(9H, s), 2.52(3H, s), 3.98–4.10(2H, m), 4.18–4.33(1H, m), 4.34–4.48(1H, m), 6.42–6.44(1H, m), 7.07(1H, d, J 3.0 Hz), 7.24–7.29(1H, d, J 10.0 Hz), 7.43–7.50(1H, m). |
| 31a | 5-F, 6-EtS (S) | mp 133° C.; IR ν$_{max}$ (Nujol)/cm$^{-1}$ 3368, 2925, 2854, 1682, 1529, 1474, 1251, 1163 and 1061; NMR δ$_H$ (400 MHz, CDCl$_3$) 1.12(3H, d, J 6.5 Hz), 1.27(3H, t, J 7.5), 1.42(9H, s), 2.94(2H, q, J 7.5 Hz)), 3.98–4.13(2H, m), 4.15–4.29 (1H, m), 4.32–4.46(1H, m), 6.43–6.44(1H, m), 7.09(1H, d, J 3.0 Hz), 7.24–7.30(1H, m), 7.47–7.53(1H, m). |
| 32a | 4-Me (S) | mp 65–66° C.; IR ν$_{max}$ (Nujol)/cm$^{-1}$; NMR δ$_H$ (400 MHz, CDCl$_3$) 1.09(3H, d, J 6.5 Hz), 1.43(9H, s), 2.54(3H, s), 4.07(2H, m), 4.26(1H, m), 6.51(1H, d, J 3 Hz), 6.90(1H, dd, J 1, 7 Hz), 7.05(1H, d, J 3 Hz), 7.11(1H, dd, J 7, 8 Hz), 7.27(1H, d, J 8 Hz). |
| 33a | 5-Br (S) | mp 115–116° C.; Found: C, 54.43; H, 5.94; N, 7.85%. C$_{16}$H$_{21}$N$_2$BrO$_2$ requires C, 54.40; H, 5.99; N, 7.93%; NMR δ$_H$ (400 MHz, CDCl$_3$) 1.08(3H, d, J 6.5 Hz), 1.42 (9H, s), 4.03(2H, m), 4.23(1H, m), 6.42(1H, d, J 3 Hz), 7.04(1H, d, J 3 Hz), 7.26(1H, d, J 1.5 Hz), 7.29(1H, m), 7.71(1H, t, J 1.5 Hz). |
| 34a | 5,6-di-OMe (S) | IR ν$_{max}$ (Nujol)/cm$^{-1}$; 3358, 2925, 2854, 1680, 1514, 1488, 1457, 1365, 1293, 1238, 1170, 1147, 1078, 1028 and 840; NMR δ$_H$ (400 MHz, CDCl$_3$) 1.12(3H, d, J 6.5 Hz), 1.43 (9H, s), 3.91(3H, s), 3.96(3H, s), 3.98(1H, m), 4.06(1H, m), 4.25(1H, m), 6.38(1H, d, J 3 Hz), 6.93(1H, d, J 3 Hz), 7.04(1H, brs.), 7.06(1H, s). |
| 35a | 4-F (S) | mp 100–101° C.; Found; C, 65.23; H, 7.05; N, 9.47% C$_{16}$H$_{22}$N$_2$FO$_2$ requires C, 65.73; N, 7.24; N, 9.58%; NMR δ$_H$ (400 MHz, CDCl$_3$) 1.11(3H, d, J 6.5 Hz), 1.43(9H, s), 4.07(2H, m), 4.26(1H, m), 6.58(1H, d, J 3 Hz), 6.76(1H, dd, J 7.5, 10 Hz), 7.03(1H, d, J 3 Hz), 7.11(1H, dt, J 5, 7.5 Hz), 7.20(1H, t, J 8 Hz). |
| 36a | 7-OMe (S) | mp 87–88° C.; NMR δ$_H$ (400 MHz, CDCl$_3$) 1.11(3H, d, J 6.5 Hz), 1.30(9H, s), 3.95(3H, s), 4.03(1H, sept, J 7 Hz), 4.36(1H, m), 4.50(1H, m), 6.44(1H, d, J 3 Hz), 6.63(1H, d, J 7.5 Hz), 6.97(1H, m), 6.98(1H, t, J 7.5 Hz), 7.20(1H, dd, J 1, 8 Hz). |
| 37a | 7-Et (S) | mp 115–116° C.; NMR δ$_H$ (400 MHz, CDCl$_3$) 1.09(3H, d, J 3 Hz), 1.33(3H, t, J 7.5 Hz), 1.39(9H, s), 3.06(2H, m), 3.98(1H, sept, J 7 Hz), 4.18(1H, dd, J7, 14 Hz), 4.36(1H, m), 6.49(1H, d, J 3 Hz), 6.99(1H, dd, J 1, 7.5 Hz), 7.01 (1H, d, J 7 Hz), 7.04(1H, d, J 7 Hz), 7.46(1H, dd, J 1, 7.5 Hz). |
| 38a | 4-Cl (S) | mp 90–91° C.; NMR δ$_H$ (400 MHz, CDCl$_3$) 1.11(3H, d, J 6.5 Hz), 1.43(9H, s), 4.08(2H, m), 4.26(1H, m), 6.61(1H, dd, J 1, 3 Hz), 7.09(1H, d, J 4 Hz), 7.10(1H, m), 7.11(1H, d, J 4 Hz), 7.35(1H, m). |
| 39a | 6-SMe (S) | NMR δ$_H$ (400 MHz, CDCl$_3$) 1.10(3H, d, J 6.6 Hz), 1.41 (9H, br s), 2.53(3H, s), 4.04–4.49(4H, br m), 6.44(1H, d, J 3.0 Hz), 7.00(1H, d, J 2.9 Hz), 7.09(1H, d, J 8.3 Hz), 7.41 (1H, s), 7.51(1H, d, J 8.3 Hz); IR (Nujol)ν$_{max}$/cm$^{-1}$ 3362, 2924, 1681, 1533, 1174, 1061 and 803; Found C, 63.26, H, 7.58, N, 8.59%. C$_{17}$H$_{24}$N$_2$O$_2$S requires C, 63.72, H, 7.55, N, 8.74%. |
| 40a | 6-SEt (S) | mp 112–113° C.; NMR δ$_H$ (400 MHz, CDCl$_3$) 1.10(3H, d, J 6.7 Hz), 1.27(3H, t, J 7.3 Hz), 1.41(9H, br s), 2.93(2H, q, J 7.2 Hz), 4.02–4.49(4H, m), 6.45(1H, d, J 3.0 Hz), 7.03 (1H, d, J 3.0 Hz), 7.14(1H, d, J 7.0 Hz), 7.47(1H, s) and 7.51(1H, d, J 8.4 Hz); IR(film)ν$_{max}$/cm$^{-1}$ 3370, 2924, 1684, 1524, 1466, 1162, 1057 and 790; Found C, 64.49, H, 8.00, N, 8.15%. C$_{18}$H$_{26}$N$_2$O$_2$S requires C, 64.64, H, 7.83, N, 8.37%. |

TABLE 7-continued

Indoles prepared using General Method B, step (a)

| No | R | Data |
|---|---|---|
| 41a | 6-SPr (S) | mp 74–75° C.; NMR $\delta_H$ (400 MHz, CDCl$_3$) 0.99(3H, t, J 7.1 Hz), 1.10(3H, d, J 6.9 Hz), 1.41(9H, br s), 1.59–1.68(2H, m), 2.89(2H, t, J 6.8 Hz), 4.02–4.40(4H, br m), 6.44(1H, d, J 3.0 Hz), 7.02(1H, d, J 3.0 Hz), 7.13(1H, d, J 8.0 Hz), 7.47(1H, s) and 7.50(1H, d, J 8.7 Hz); IR(Nujol)$\nu_{max}$/cm$^{-1}$ 3357, 2927, 1686, 1534, 1460, 1377, 1175, 1062 and 810. |
| 42a | 6-S$^i$Pr (S) | mp 74–75° C.; NMR $\delta_H$ (400 MHz, CDCl$_3$) 1.11(3H, d, J 6.6 Hz), 1.27(6H, d, J 6.9 Hz), 1.42(9H, br s), 3.30–3.34(1H, m), 4.04–4.50(4H, br m), 6.48(1H, d, J 3.5 Hz), 7.07(1H, d, J 3.1 Hz), 7.19(1H, d, J 9.6 Hz) and 7.53(2H, m); IR (Nujol)$\nu_{max}$/cm$^{-1}$ 3374, 2926, 1690, 1515, 1463, 1174, 1080 and 813. |

TABLE 8

Indolines prepared using General Method B, step (b)

| No | R | Data |
|---|---|---|
| 10b | 6-Cl (S) | NMR $\delta_H$(400 MHz, CDCl$_3$) 1.24(3H, d, J 8 Hz), 1.46(9H, s), 2.97(1H, t, J 8 Hz), 3.04–3.10(1H, m), 3.45–3.56(1H, m), 3.88–3.98(1H, m), 4.52(1H, brs), 6.42(1H, brs), 6.58–6.62(1H, m) and 6.95–7.01(1H, m). |
| 11b | 7-OBn (RS) | IR $\nu_{max}$ (Nujol)/cm$^{-1}$ 3368, 1683, 1536, 1461, 1369, 1249, 1170, 1059 and 743; NMR $\delta_H$ (400 MHz, CDCl$_3$), 0.96(3H, d, J 6.5 Hz), 1.36(9H, br s), 2.89–3.13(3H, m), 3.21–3.35(1H, m), 3.45–3.87(3H, m), 5.04(2H, s), 6.63(1H, t, J8 Hz), 6.75(2H, d, J 8 Hz) and 7.3–7.45(5H, m). |
| 12b | 6-Br (S) | IR $\nu_{max}$ (Nujol)/cm$^{-1}$ 1679, 1604, 1503, 1360, 1169, 1014 and 775; NMR $\delta_H$ (400 MHz, CDCl$_3$) 1.21(3H, d, J 6.5 Hz), 1.43(9H, s), 2.88–3.06(1H, m), 3.41–3.53(2H, m), 3.85–3.93(2H, m), 4.47(1H, brs), 6.52–6.54(1H, m), 6.70–6.74(1H, m) and 6.87–6.89(1H, m). |
| 13b | 6-OMe (S) | IR $\nu_{max}$ (Nujol)/cm$^{-1}$ 1687, 1622, 1529, 1460, 1285, 1173, 1059 and 812; NMR $\delta_H$(400 MHz, CDCl$_3$) 1.25(3H, d, J 6 Hz), 1.50(9H, s), 2.85–2.95(2H, m), 2.9–3.1(2H, m), 3.33–3.52(2H, m), 3.80(3H, s), 3.85–3.95(1H, m), 4.45–4.49(1H, brs), 6.1(1H, brs), 6.16–6.18(1H, m) and 6.93–6.95(1H, m). |
| 14b | 5-Me, 6-Cl (S) | IR $\nu_{max}$ (Nujol)/cm$^{-1}$ 1684, 1533, 1462, 1291, 1058 and 816; NMR $\delta_H$ (400 MHz, CDCl$_3$) 1.19(3H, d, J 7.5 Hz), 1.42(9H, s), 2.42(3H, s), 2.86–2.91(1H, m), 2.96–3.0(1H, m), 3.33–3.44(4H , m), 3.86–3.91(1H, m), 4.46(1H, brs), 6.41(1H, s) and 6.87(1H, s). |
| 15b | 5-F, 6-Cl (R) | IR $\nu_{max}$ (Nujol)/cm$^{-1}$ 1678, 1541, 1457, 1058 and 733; NMR $\delta_H$ (400 MHz, CDCl$_3$) 1.17(3H, d, J 6.5 Hz), 1.39(9H, s), 2.90–3.01(4H, m), 3.40–3.50(3H, m), 3.84–3.91(1H, m), 4.43(1H, brs), 6.33(1H, d, J 6 Hz) and 6.79(1H, d, J 6 Hz) |
| 16b | 5F, 6-Cl (S) | IR $\nu_{max}$ (Nujol)/cm$^{-1}$ 1677, 1540, 1501, 1170, 1058 and 732; NMR $\delta_H$ (400 MHz, CDCl$_3$) 1.17(3H, d, J 6.5 Hz), 1.39(9H, s), 2.90–3.01 (4H, m), 3.40–3.50(3H, m), 3.84–3.91(1H, m), 4.43(1H, brs), 6.33(1H, d, J 6 Hz) and 6.79 (1H, d, J 6 Hz) |

TABLE 8-continued

Indolines prepared using General Method B, step (b)

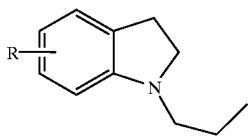

| No | R | Data |
|---|---|---|
| 17b | 5-F, 7-Cl (S) | IR ν$_{max}$ (Nujol/cm$^{-1}$ 1684, 1532, 1249, 1173, 1057, 839 and 643; NMR δ$_H$ (400 MHz, CDCl$_3$) 1.21(3H, d, J 6.5 Hz), 1.39(9H, s), 2.96–3.05(2H, m), 3.26–3.34(1H, m), 3.48(1H, dd, J 14, 8 Hz), 3.57–3.66(1H, m), 3.92–3.99(1H, m), 4.61(1H, brs) and 6.77–6.69(2H, m). |
| 18b | 6-Br (R) | IR ν$_{max}$ (Nujol)/cm$^{-1}$ 1679, 1604, 1537, 1503, 1361, 1169, 1014 and 775; NMR δ$_H$ (400 MHz, CDCl$_3$) 1.21(3H, d, J 6 Hz), 1.42(9H, s), 2.88–3.07(4H, m), 3.38–3.54(2H, m), 3.84–3.94(1H, m), 4.47(1H, brs), 6.52–6.54(1H, m), 6.70–6.75(1H, m) and 6.85–6.89(1H, m). |
| 19b | 7-Br (R) | IR ν$_{max}$ (Nujol)/cm$^{-1}$ 1689, 1603, 1526, 1366, 1175, 1051 and 748; NMR δ$_H$ (400 MHz, CDCl$_3$) 1.23(3H, d, J 6.5 Hz), 1.38(9H, s), 3.0(2H, t, J 8.5 Hz), 3.14–3.39(1H, m), 3.43–3.51(1H, m), 3.58–3.67(1H, m), 3.74–3.81(1H, m), 3.96–4.04(1H, m), 4.69(1H, brs), 6.52–6.54(1H, t, J 7.5 Hz), 6.97(1H, d, J 7.5 Hz) and 7.17(1H, d, 17.5 Hz). |
| 20b | 7-Br (S) | IR ν$_{max}$ (Nujol)/cm$^{-1}$ 1683, 1531, 1465, 1251, 1173, 1056 and 745; NMR δ$_H$ (400 MHz, CDCl$_3$) 1.20(3H, d, J 7 Hz), 1.35(9H, s), 3.28–3.37(1H, m), 3.40–3.48(1H, m), 3.54–3.64(2H, m), 3.92–4.0(2H, m), 4.67(1H, brs), 6.49(1H, t, J 8 Hz), 6.93–6.96(1H, m) and 7.14(1H, dd, J 8.5, 1 Hz). |
| 21b | 6,7-dichloro (R) | IR ν$_{max}$ (Nujol)/cm$^{-1}$ 1684, 1533, 1462, 1250, 1059 and 778; NMR δ$_H$ (400 MHz, CDCl$_3$) 1.21(3H, d, J 6 Hz), 1.35(9H, s), 2.94–3.01(2H, m), 3.50–3.86(5H, m), 4.59 (1H, brs), 6.74–6.77(1H, m) and 6.81–6.84(1H, m). |
| 22b | 5,6-difluoro (S) | IR ν$_{max}$ (Nujol)/cm$^{-1}$ 1679, 1536, 1505, 1254, 1056 and 748; NMR δ$_H$ (400 MHz, CDCl$_3$) 1.24(3H, d, J 6.5 Hz), 1.46(9H, s), 2.90–3.07(4H, m), 3.39–3.55(2H, m), 3.80–3.89(1H, m), 4.50(1H, brs), 6.27(1H, dd, J 10.5 6 Hz) and 6.85–6.90(1H, m). |
| 23b | 6,7-dichloro (S) | IR ν$_{max}$ (Nujol)/cm$^{-1}$ 1683, 1601, 1534, 1463, 1250, 1060 and 778; NMR δ$_H$ (400 MHz, CDCl$_3$) 1.20(3H, d, J 6.5 Hz), 1.36(9H, s), 2.94–3.00(2H, m), 3.49–3.56(2H, m), 3.97–4.03(3H, m), 4.58(1H, brs), 6.74(1H, d, J 7.5 Hz) and 6.82(1H, d, J 7.5 Hz). |
| 24b | 6-CF$_3$ (S) | IR ν$_{max}$ (Nujol)/cm$^{-1}$ 1679, 1540, 1463, 1159, 1115, 799 and 659; NMR δ$_H$ (400 MHz, CDCl$_3$) 1.23(3H, d, J 6 Hz), 1.41(9H, s), 3.0–3.11(4H, m), 3.44–3.59(2H, m), 3.92–3.98 (1H, m), 4.48(1H, brs), 6.59(1H, brs), 6.87(1H, d,J 9 Hz) 7.10(1H, d,J 6.5 Hz). |
| 25b | 5-F, 6-Br (S) | IR ν$_{max}$ (Nujol)/cm$^{-1}$ 1667, 1539, 1500, 1267, 1169, 1057 and 730; NMR δ$_H$ (400 MHz, CDCl$_3$) 1.2 (3H, d, J 7 Hz), 1.44(9H, s), 2.92(1H, m), 3.0(1H, dd, J 8.5, 5.5 Hz), 3.84–3.92(2H, m), 4.48(1H, brs), 6.51(1H, d, J 4.5 Hz) and 6.83 (1H, d, J 8 Hz). |
| 26b | 6-CF$_3$ (R) | IR ν$_{max}$ (Nujol)/cm$^{-1}$ 1679, 1618, 1540, 1159, 1016, 799 and 659; NMR δ$_H$ (400 MHz, CDCl$_3$) 1.20(3H, d, J 6 Hz), 1.38 (9H, s), 3.0(1H, t, J 8 Hz), 3.08(2H, d, J 7 Hz), 3.43–3.57 (2H, m), 3.88–3.96(1H, m), 4.44(1H, brs), 7.53(1H, brs), 6.86(1H, d, J 7 Hz) and 7.07(1H, d, J 7 Hz). |
| 27b | 6-Cl, 7-F(S) | IR ν$_{max}$ (Nujol)/cm$^{-1}$ 1681, 1557, 1400, 1313, 1263, 1206, 926 and 678; NMR δ$_H$ (400 MHz, CDCl$_3$) 1.18(3H, d, J 7 Hz) 1.38(9H, s) 2.59–3.02(2H, m) 3.21(1H, dd, J 14, 5 Hz) 3.39–3.49(2H, m) 3.61–3.69(2H, m) 4.45–4.53(1H, brs) 6.55–6.60(1H, m) 6.68–6.71(1H, m) |
| 28b | 5-Cl (S) | IR ν$_{max}$ (Nujol)/cm$^{-1}$ 1683, 1529, 1490, 1461, 1245, 1168 and 807; NMR δ$_H$ (400 MHz, CDCl$_3$) 1.21(3H, d, J7 Hz), 1.44(9H, s), 2.93–3.09(4H, m), 3.38–3.51(2H, m), 3.84–3.92(1H, m), 4.49(1H, brs), 6.36(1H, d, J 7 Hz) and 6.97–7.01(2H, m). |
| 29b | 5-F (S) | IR ν$_{max}$ (Nujol)/cm$^{-1}$ 1687, 1538, 1464, 1235, 1169, 867 and 796; NMR δ$_H$ (400 MHz, CDCl$_3$) 1.25(3H, d, J 6.5 Hz), 1.47(9H, s), 2.95–3.08(1H, m), 3.40(1H, dd, J 16, 8.5 Hz), 3.47(1H, dd, J 16, 8.5 Hz), 3.87–3.95(1H, m), 4.57 (1H, brs), 6.39(1H, dd, J 8, 3.5 Hz), 6.76(1H, td, J 8.5, 2 Hz) and 6.81–6.85(1H, m). |

TABLE 8-continued

Indolines prepared using Gerieral Method B, step (b)

| No | R | |
|---|---|---|
| 30b | 5-F, 6-MeS (S) | mp 96–100° C.; IR $\nu_{max}$ (Nujol)/cm$^{-1}$ 3364, 2924, 2854, 1678, 1611, 1528, 1500, 1455, and 1163; NMR $\delta_H$ (400 MHz, CDCl$_3$) 1.23(3H, d, J 7.0 Hz), 1.44(9H, s), 2.44(3H, s), 2.88–2.99(3H, m), 3.05(1H, dd, J 13.5, 5.5 Hz), 3.37 (1H, q, J 8.5 Hz), 3.46(1H, q, J 8.5 Hz), 3.83–3.95(1H, m), 4.42–4.62(1H, brm), 6.42(1H, d, J 6.0 Hz), 6.77–6.81(1H, m). |
| 31b | 5-F, 6-EtS (S) | IR $\nu_{max}$ (Nujol)/cm$^{-1}$ 3363, 2970, 2927, 1688, 1495, 1366, 1248, 1169, and 1057; NMR $\delta_H$ (400 MHz, CDCl$_3$) 1.23 (3H, d, J 6.5 Hz), 1.27(3H, t, J 7.0 Hz), 1.44(9H, s), 2.84–3.07(6H, m), 3.38(1H, q, J 8.5 Hz), 3.46(1H, q, J 8.5 Hz), 3.82–3.95(1H, m), 4.41–4.61(1H, brm), 6.46(1H, d, J 6.5 Hz), 6.80(1H, d, J 9.0 Hz). |
| 32b | 4-Me (S) | mp 75–76° C.; Found: C, 69.91; H, 9.01; N, 9.56%. C$_7$H$_{26}$N$_2$O$_3$ requires C, 70.31; H, 9.02; N, 9.64%; NMR $\delta_H$ (400 MHz, CDCl$_3$) 1.23(3H, d, J 6.5 Hz), 1.44(9H, s), 2.20(3H, s), 2.92(2H, t, J 8.5 Hz), 3.03(1H, dd, J 6, 13.5 Hz), 3.08(1H, dd, J 6, 14 Hz), 3.42(1H, q, J, 8.5 Hz), 3.48 (1H, q, J 8.5 Hz), 3.90(1H, sept, J 6.5 Hz), 6.35(1H, d, J 7.5 Hz), 6.52(1H, d, J 7.5 Hz), 6.98(1H, t, J 7.5 Hz). |
| 33b | 5-Br (S) | Found: C, 54.06; H, 6.53; N, 7.66%. C$_{16}$H$_{23}$N$_2$BrO$_2$ requires C, 54.09; H, 6.53; N, 7.88%; NMR $\delta_H$ (400 MHz, CDCl$_3$) 1.21(3H, d, J 6.5 Hz), 1.42(9H, s), 2.97(2H, t, J 8.5 Hz), 2.98(1H, m), 3.08(1H, dd, J 6, 14 Hz), 3.42(1H, q, J, 8.5 Hz), 3.45(1H, sept, J 8.5 Hz), 3.88(1H, m), 6.35 (1H, d, J 8.5 Hz), 7.1 l(1H, m), 7.14(1H, m). |
| 34b | 5,6-di-OMe (S) | IR $\nu_{max}$ (Nujol)/cm$^{-1}$ 3359, 2974, 2933, 2835, 1694, 1617, 1054, 1455, 1366, 1235, 1206, 1169, 1088, 1059, 1022, 843 and 748; NMR $\delta_H$ (400 MHz, CDCl$_3$) 1.26(3H, d, J 6.5 Hz), 2.95(3H, m), 3.06(1H, m), 3.41(2H, m), 3.81 (3H, s), 3.86(3H, s), 3.87(1H, m), 6.30(1H, brs.), 6.75 (1H, s). |
| 35b | 4-F (S) | IR $\nu_{max}$ (Nujol)/cm$^{-1}$ 3345, 2925, 2854, 1602, 1632, 1534, 1469, 1364, 1253, 1226, 1169, 1057, 1024 and 748; NMR $\delta_H$ (400 MHz, CDCl$_3$) 1.22(3H, d, J 6.5 Hz), 1.43(9H, s), 3.03(2H, t, J 8.5 Hz), 3.10(2H, dt, J 6, 14 Hz), 3.50(2H, sept, J 8.5 Hz), 3.90(1H, m), 6.26(1H, d, J 8 Hz), 6.36(1H, t, J 8.5 Hz), 7.00(1H, dt, J 5.5, 8.5 Hz). |
| 36b | 7-OMe (S) | mp 108°–109° C.; NMR $\delta_H$ (400 MHz, CDCl$_3$) 1.20(3H, d, J 6.5 Hz), 1.39(9H, s), 3.01(2H, m), 3.20(1H, dd, J 5, 13 Hz), 3.39(1H, q, J 8.5 Hz), 3.59(2H, m), 3.82(3H, s), 3.88 (1H, m), 6.68 to 6.78(3H, m). |
| 37b | 7-Et (S) | mp 81–82° C.; NMR $\delta_H$ (400 MHz, CDCl$_3$) 1.26(3H, t, J 7.5 Hz), 1.28(3H, d, J 6.5 Hz), 1.44(9H, s), 2.67(2H, q, J 7.5 Hz), 3.05(3H, m), 3.19(1H, dd, J 7.5, 13.5 Hz), 3.48(2H, m), 3.90(1H, m), 6.81(1H, m), 6.95(1H, d, J 7.5 Hz), 6.99 (1H, d, J 7.5 Hz). |
| 38b | 4-Cl (S) | NMR $\delta_H$ (400 MHz, CDCl$_3$) 1.22(3H, d, J 6.5 Hz), 1.43 (9H, s), 3.65(2H, t, J 8.5 Hz), 3.11(2H, m), 3.50(1H, q, J 8.5 Hz), 3.58(1H, m), 3.91(1H, m), 6.39(1H, m), 6.65(1H, m), 7.00(1H, t, J 7.5 Hz); HPLC(Column: Supelcosil ABZ$^+$ [170 mm × 4.6 mm], particle size 5 $\mu$M; Eluent: methanol, 10 mM aqueous ammonium acetate solution (7:3); Flow Rate 1.0 mL/min; Detection Wavelength $\lambda$ = 210 nM) Retention Time: 4.55 min. |
| 39b to 42b | | intermediates used immediately |

TABLE 9

Examples 10–42. Indolines prepared using General Method B, step (c)

| No | Structure | Data |
|----|-----------|------|
| 10 | 6-chloro-indoline with N-CH₂CH(CH₃)NH₂ (Chiral) | Fumarate. mp 164° C.(dec.); Found C, 56.35; H, 6.12; N, 9.30%. $C_{18}H_{15}ClN_2 \cdot 0.75\ C_4H_4O_4$ requires: C, 56.47; H, 6.09; N, 9.41%. |
| 11 | 7-benzyloxy-indoline with N-CH₂CH(CH₃)NH₂ | Trifluoroacetate. mp 201–203° C.; Found: C, 60.57; H, 5.86; N, 6.99%. $C_{15}H_{22}N_2O \cdot CF_3CO_2H$ requires: C, 60.60; H, 5.85; N, 7.06%; IR $\nu_{max}$ (Nujol)/cm$^{-1}$ 1676, 1464, 1204, 1135, 1057, 841, 754 and 724; NMR $\delta_H$ (400 MHz, DMSO-d6), 0.93,(3H, d, J 6.5 Hz), 2.82–2.98(2H, m), 3.09–3.18(1H, m), 3.23–3.5(4H, m), 5.07(2H, s), 6.63(1H, t, J 8 Hz), 6.72 (1H, d, J 7.5 Hz), 6.82(1H, d, J 7 Hz), 7.29–7.49(5H, m) and 7.76–8.01(3H, br s). |
| 12 | 6-bromo-indoline with N-CH₂CH(CH₃)NH₂ (Chiral) | Fumarate. mp 191–192° C.; Found: C, 49.51; H, 5.48; N, 8.59%. $C_{11}H_{15}BrN_2 \cdot 0.6\ C_4H_4O_4$ requires: C, 49.55; H, 5.40; N, 8.62%. |
| 13 | 6-methoxy-indoline with N-CH₂CH(CH₃)NH₂ (Chiral) | Fumarate. mp 175–6° C.; IR $\nu_{max}$ (Nujol/cm$^{-1}$) 1623, 1568, 1525, 1497, 1462, 1379, 1343, 1276, 1196, 1176, 1097 and 666; NMR $\delta_H$ (400 MHz, DMSO-d$_6$) 1.19(3H, d, J 7.5 Hz), 2.78–2.87(2H, m), 2.87–2.96(2H, m), 3.07–3.17(2H, m), 3.22–3.31(1H, m), 3.39–3.49(1H, m) 3.70(3H, s), 6.1–6.15 (1H, m), 6.17–6.21(1H, m) and 6.83–6.93(1H,m). |
| 14 | 6-chloro-5-methyl-indoline with N-CH₂CH(CH₃)NH₂ (Chiral) | Fumarate. mp 172–174° C.; NMR $\delta_H$ (400 MHz, DMSO-d$_6$) 1.52(3H, d, J 6.5 Hz), 2.49(3H, s), 3.28(1H, dd, J 13, 5.5 Hz) 3.5–3.85(6H, m), 6.93(1H, s) and 7.31(1H, s). |
| 15 | 5-fluoro-6-chloro-indoline with N-CH₂CH(CH₃)NH₂ (Chiral) | Fumarate. mp 198–200° C.; NMR $\delta_H$ (400 MHz, DMSO-d$_6$) 1.19(3H, d, J 7 Hz) 2.82–3.01(2H, m) 3.18–3.38(3H, m) 3.46–3.54(1H, m) 6.69(1H, d, J 7 Hz) 7.08(1H, d, J 7 Hz) |
| 16 | 5-fluoro-6-chloro-indoline with N-CH₂CH(CH₃)NH₂ (Chiral) | NMR $\delta_H$ (400 MHz, DMSO-d$_6$) 1.12(3H, d, J 7.5 Hz), 2.91–2.98(2H, m), 3.07(1H, dd, J 7.5 Hz), 3.26–3.34(1H, m), 3.33–3.40(1H,m), 3.50–3.59(2H, m), 6.65(1H, d, J 7 Hz) and 7.09(1H, d, J 7 Hz). |

TABLE 9-continued

Examples 10–42.Indolines prepared using General Method B, step (c)

| No | Structure | Data |
|---|---|---|
| 17 | 5-F, 7-Cl indoline, N-CH2CH(CH3)NH2, Chiral | Fumarate. mp 195–196° C.; NMR $\delta_H$ (400 MHz, DMSO-d$_6$) 1.12(3H, d, J 6.5 Hz), 2.93–2.99(1H, m), 3.15–3.51(6H, m) and 6.91–6.98(2H, m). |
| 18 | 6-Br indoline, N-CH2CH(CH3)NH2, Chiral | Fumarate. mp 193–194° C.; NMR $\delta_H$ (400 MHz, DMSO-d$_6$) 1.13(3H, d, J 6.5 Hz), 2.82–2.90(1H, m), 2.94(1H, dd, J 13.5, 5 Hz), 3.10–3.18(1H, dd, J 13.5, 8 Hz), 3.21–3.37(2H, m), 3.45–3.53(2H, m), 6.65–6.69(2H, m) and 6.93(1H, d, J 7.5 Hz). |
| 19 | 7-Br indoline, N-CH2CH(CH3)NH2, Chiral | Fumarate. mp 197° C.; NMR $\delta_H$ (400 MHz, DMSO-d$_6$) 1.19(3H, d, J 6.5 Hz), 2.93–3.0(2H, m), 3.30–3.57(5H m), 6.56(1H, dd, J 8, 7 Hz), 7.05(1H, dd, J 7, 1 Hz) and 7.15 (1H, dd, J 8, 1 Hz). |
| 20 | 7-Br indoline, N-CH2CH(CH3)NH2, Chiral | Fumarate. mp 202–204° C.; NMR $\delta_H$ (400 MHz, DMSO d$_6$) 1.13(3H, d, J 6.5 Hz), 2.93–3.56(7H, m), 6.54(1H, t, J 7.5 Hz), 7.02–7.05(1H, m) and 7.15(1H, dd, J 7.5, 1 Hz). |
| 21 | 6,7-diCl indoline, N-CH2CH(CH3)NH2, Chiral | Fumarate. mp 213–214° C. ; NMR $\delta_H$ (400 MHz, DMSO-d6) 1.11(3H, d, J 6 Hz), 2.91–2.97(1H, m), 3.22–3.63(6H, m), 6.82(1H, d, J 8 Hz) and 6.98(1H, d, J 8 Hz). |
| 22 | 5,6-diF indoline, N-CH2CH(CH3)NH2 | Fumarate. mp 165° C.(dec.); NMR $\delta_H$ (400 MHz, DMSO-d6) 1.21(3H, d, J 6.5 Hz), 2.84–2.93(2H, m), 2.99(1H, dd, J 13, 5 Hz), 3.22(1H, dd, J 13, 8 Hz), 3.28–3.41(2H, m), 3.48–3.56(1H, m), 6.64(1H, dd, J, 12, 6.5 Hz) and 7.08–7.13(1H, m). |
| 23 | 6,7-diCl indoline, N-CH2CH(CH3)NH2, Chiral | Fumarate. mp 176–178° C. ; NMR $\delta_H$ (400 MHz, DMSO-d6) 1.16(3H, d, J 6.5 Hz), 2.94–3.00(1H, m), 3.29–3.63 (6H, m), 6.85(1H, d, J 8 Hz) and 7.01(1H, d, J 8 Hz). |

TABLE 9-continued

Examples 10–42.Indolines prepared using General Method B, step (c)

| No | Structure | Data |
|---|---|---|
| 24 | Chiral; 6-CF₃-indoline, N-CH₂CH(CH₃)NH₂ | Fumarate. mp 197–199° C.; NMR δ$_H$ (400 MHz, DMSO-d$_6$) 1.19(3H, d, J 6 Hz), 2.99–3.06(2H, m), 3.35–3.62(5H, m), 6.79(1H, brs), 6.89(1H, d, J 7.5 Hz) and 7.20(1H, d, J 7.5 Hz). |
| 25 | 5-F, 6-Br-indoline, N-CH₂CH(CH₃)NH₂ | Fumarate. mp 195–196° C.; NMR δ$_H$ (400 MHz, DMSO-d$_6$) 1.18(3H, d, J 6.5 Hz), 2.86–2.92(2H, m), 2.96(1H, dd, J 14, 5 Hz), 3.15–3.23(2H, m), 3.37–3.26(1H, m), 3.47–3.54 (1H, m), 6.78(1H, d, J 6 Hz) and 7.07(1H, d, J 8.5 Hz). |
| 26 | 6-CF₃-indoline, N-CH₂CH(CH₃)NH₂ | Fumarate. mp 196–197° C.; NMR δ$_H$ (400 MHz, DMSO-d$_6$) 1.14(3H, d, J 6 Hz), 2.95–3.01(1H, m), 3.14–3.58(6H, m), 6.75(1H, brs), 6.85(1H, d, J 8 Hz) and 7.17(1H, d, J 8 Hz). |
| 27 | Chiral; 6-Cl, 7-F-indoline, N-CH₂CH(CH₃)NH₂ | Fumarate. NMR δH (400 MHz, DMSO-d$_6$) 1.14(3H, d, J 6 Hz), 2.98–3.03(1H, m), 3.19–3.56(6H, m), 6.73(1H, dd, J 6.5, 6 Hz) and 6.90(1H, d, J 8 Hz). |
| 28 | Chiral; 5-Cl-indoline, N-CH₂CH(CH₃)NH₂ | Fumarate. mp 207–210° C. ; NMR δ$_H$ (400 MHz, DMSO-d6) 1.13(3H, d, J 6.5 Hz), 2.89–2.98(2H, m), 3.05–3.51 (5H, m), 6.52(1H, d, J 8 Hz) and 7.05–7.07(2H, m). |
| 29 | Chiral; 5-F-indoline, N-CH₂CH(CH₃)NH₂ | Fumarate. mp 175–176° C. ; NMR δ$_H$ (400 MHz, DMSO-d6) 1.23(3H, d, J 6.5 Hz), 2.87–2.99(2H, m), 3.33–3.41 (2H, m), 3.43–3.51(3H, m), 6.54(1H, dd, J 8.5, 4.5 Hz), 6.82(1H, td, J 8.5, 2.5 Hz) and 6.94(1H, dd, J 8.5, 2.5 Hz). |
| 30 | 5-F, 6-MeS-indoline, N-CH₂CH(CH₃)NH₂ | Fumarate. mp 96–100° C.; IR ν$_{max}$ (Nujol)/cm$^{-1}$ 3364, 2924, 2854, 1678, 1611, 1528, 1500, 1455, and 1163; NMR δ$_H$ (400 MHz, CDCl$_3$) 1.23(3H, d, J 7.0 Hz), 1.44(9H, s), 2.44 (3H, s), 2.88–2.99(3H, m), 3.05(1H, dd, J 13.5, 5.5 Hz), 3.37(1H, q, J 8.5 Hz), 3.46(1H, q, J 8.5 Hz), 3.83–3.95 (1H, m), 4.42–4.62(1H, brm), 6.42(1H, d, J 6.0 Hz), 6.77–6.81(1H, m). |

TABLE 9-continued

Examples 10–42.Indolines prepared using General Method B, step (c)

| No | Structure | Data |
|---|---|---|
| 31 | (5-F, 6-EtS indoline with N-CH2CH(CH3)NH2) | Fumarate. mp 164–168° C.; IR $\nu_{max}$ (Nujol)/cm$^{-1}$ 2924, 1702, 1626, 1458, 1378, 1227, 1041, 791 and 652; NMR $\delta_H$ (400 MHz, DMSO-d$_6$) 1.19(3H, t, J 7.0 Hz), 1.22(3H, d, J 6.5 Hz), 2.81–3.01(5H, m), 3.19–3.31(2H, m), 3.32–3.41 (1H, m), 3.45–3.54(1H, m), 6.44(2H, s), 6.59(1H, d, J 6.5 Hz), 6.95(1H, d, J 9.5 Hz), 8.00–10.31(3H, brm). |
| 32 | Chiral (4-methyl indoline with N-CH2CH(CH3)NH2) | Fumarate. mp 161–162° C.; NMR $\delta_H$ (400 MHz, DMSO-d$_6$) 1.23(3H, d, J 6.5 Hz), 2.14(3H, s), 2.85(2H, m), 2.99(1H, dd, J 5.5, 13.5 Hz), 3.22(1H, dd, J 5.5, 13.5 Hz), 3.30(1H, t, J 8.5 Hz), 3.36(1H, m), 3.47(1H, dt, J 6.5, 8.5 Hz), 6.40 (1H, d, J 8 Hz), 6.45(2H, s), 6.46(1H, d, J 8 Hz), 6.92(1H, t, J 8 Hz); Found: C, 59.37; H, 7.32 $C_{16}H_{22}N_2O_4 \cdot H_2O$ requires C, 59.24; H, 7.46; N, 8.64%. |
| 33 | Chiral (5-Br indoline with N-CH2CH(CH3)NH2) | Fumarate. NMR $\delta_H$ (400 MHz, DMSO-d$_6$) 1.23(3H, d, J 6.5 Hz), 2.94(2H, m), 3.02(1H, dd, J 5.5, 14 Hz), 3.23(1H, dd, J 5.5, 13.5 Hz), 3.31(1H, t, J 8.5 Hz), 3.38(1H, m), 3.50(1H, dt, J 7, 8.5 Hz), 6.46(2H, s), 6.53(1H, d, J 8.5 Hz), 7.14(1H, dd, J 2.5, 8.5 Hz), 7.19(1H, d, J 2.5 Hz); Found: C, 48.51; H, 5.16; N, 7.46%. $C_{15}H_{19}BrN_2O_4$ requires C, 48.53; H, 5.16; N, 7.54%. |
| 34 | Chiral (5,6-dimethoxy indoline with N-CH2CH(CH3)NH2) | Fumarate. mp 166–167° C.(dec.); NMR $\delta_H$ (400 MHz, DMSO-d$_6$) 1.26(3H, d, J 6.5 Hz), 2.84(2H, m), 2.93(1H, dd, J 5, 13.5 Hz), 3.29(1H, dd, J 5, 13.5 Hz), 3.38(1H, m), 3.45(1H, dt, J 8.5, 5.5 Hz), 3.65(3H, s), 3.73(3H, s), 6.42 (1H, s), 6.46(2H, s), 6.78(1H, s); Found: C, 56.52; H, 6.91; N, 7.63%. $C_{17}H_{24}N_2O_6 \cdot 0.5H_2O$ requires C, 56.50; H, 6.97; N, 7.75%. |
| 35 | (4-F indoline with N-CH2CH(CH3)NH2) | Fumarate. mp 167–168° C.; NMR $\delta_H$ (400 MHz, DMSO-d$_6$) 1.23(3H, d, J 6.5 Hz), 2.96(2H, m), 3.06(1H, dd, J 5.5, 13.5 Hz), 3.28(1H, dd, J 7.5, 13.5 Hz), 3.40(2H, m), 3.56 (1H, m), 6.40(1H, t, J 8.5 Hz), 6.38–6.43(2H, m), 6.46(2H, s), 7.03(1H, dt, J 6,8 Hz); Found: C, 58.03; H, 6.18; N, 9.01%. $C_{15}H_{19}N_2FO_4$ requires C, 58.06; H, 6.17; N, 9.02%. |
| 36 | (7-methoxy indoline with N-CH2CH(CH3)NH2) | Fumarate. mp 155–156° C.(dec.); NMR $\delta_H$ (400 MHz, DMSO-d$_6$) 1.23(3H, d, J 6 Hz), 2.92(2H, t, J 9 Hz), 3.36 (5H, m), 3.75(3H, s), 6.45(2H, s), 6.66(1H, t, J 7.5 Hz), 6.73(1H, dd, J 1, 7.5 Hz), 6.76(1H, d, J 7.5 Hz). |

TABLE 9-continued

Examples 10–42. Indolines prepared using General Method B, step (c)

| No | Structure | Data |
|---|---|---|
| 37 | (7-ethyl indoline with N-CH2-CH(CH3)-NH2 chain) | Fumarate. mp 182–183° C.; NMR δ$_H$ (400 MHz, DMSO-d$_6$) 1.17(3H, t, J 7.5 Hz), 1.28(3H, d, J 6.5 Hz), 2.63(2H, m), 2.93(2H, m), 3.10(1H, dd, J 7, 13 Hz), 3.21(1H, dd, J 5.5, 13 Hz), 3.35(2H, m), 6.45(2H, s), 6.72(1H, t, J 7.5 Hz), 6.89(1H, d, J 7.5 Hz), 6.95(1H, dd, J 1, 7.5 Hz). |
| 38 | (4-chloro indoline with N-CH2-CH(CH3)-NH2 chain) | Hemi-fumarate. mp 190–192° C.; NMR δ$_H$ (400 MHz, DMSO-d$_6$) 1.14(3H, d, J 6.5 Hz), 2.96(2H, m), 3.13(1H, dd, J 8, 14 Hz), 3.25(1H, m), 3.41(1H, q, J 8.5 Hz), 3.54 (2H, dd, J 7, 8.5 Hz), 6.41(1H, s), 6.48(1H, d, J 8 Hz), 6.58 (1H, d, J 8 Hz), 7.01(1H, t, J 8 Hz). |
| 39 | Chiral (6-methylthio indoline with N-CH2-CH(CH3)-NH2 chain) | Fumarate. mp.darkens 165° C., melts 167–168° C.; NMR δ$_H$ (400 MHz, DMSO-d$_6$) 1.22(3H, d, J 6.4 Hz), 2.42(3H, s), 2.86–289(2H, m), 2.97–3.02(1H, dd, J 13.8, 5.3 Hz), 3.25–3.49(4H, m), 6.43(2H, s), 6.48–6.50(2H, m) and 6.96; IR (Nujol)ν$_{max}$/cm$^{-1}$ 2920, 1706, 1464, 979 and 652. |
| 40 | Chiral (6-ethylthio indoline with N-CH2-CH(CH3)-NH2 chain) | Fumarate. mp.darkens 140° C., melts 146–147° C.; NMR δ$_H$ (400 MHz, DMSO-d$_6$) 1.17–1.23(6H, m), 2.83–2.94(4H, m), 2.97–3.02(1H, dd, J 14.0, 5.6 Hz), 3.22–3.53(4H, m), 6.45(2H, s), 6.56(2H, m) and 6.97(1H, d, J 7.4 Hz); IR (Nujol)ν$_{max}$/cm$^{-1}$ 2924, 1676, 1463, 1377, 1278 and 650. |
| 41 | Chiral (6-propylthio indoline with N-CH2-CH(CH3)-NH2 chain) | Fumarate. mp.147–148° C.; NMR δ$_H$ (400 MHz, DMSO-d$_6$) 0.94(3H, t, J 7.0 Hz), 1.22(3H, d, J 6.0 Hz), 1.50–1.57(2H, m), 2.83–2.91(4H, m), 3.00(1H, dd, J 13.5, 5.1 Hz), 3.23–3.51(4H, m), 6.44(2H, s), 6.54–6.56(2H, m), 6.95(1H, d, J 8.1 Hz); IR(Nujol)ν$_{max}$/cm$^{-1}$ 2925, 1706, 1604, 1464, 957 and 652. |
| 42 | Chiral (6-isopropylthio indoline with N-CH2-CH(CH3)-NH2 chain) | Fumarate. mp.164–165° C.; NMR δ$_H$ (400 MHz, DMSO-d$_6$) 1.18–1.23(9H, m), 2.86–3.03(3H, m), 3.26–3.51(5H, m), 6.44(2H, s), 6.49–6.61(2H, m), 6.98(1H, d, J 7.5 Hz); IR (Nujol)ν$_{max}$/cm$^{-1}$ 2924, 1725, 1598, 1461, 1312, 880, 790 and 636. |

Indole Syntheses
6-Chloro-5-fluoro-1H-indole
2-Fluoro-4-methyl-5-nitroaniline

Concentrated nitric acid (20 g) was added dropwise over 90 min to a stirred solution of 2-fluoro-4-methylaniline (25 g, 200 mmol) in concentrated sulfuric acid (250 mL) at −10° C. The mixture was poured onto ice (1 L) and the solution adjusted to pH 13 using solid sodium hydroxide (CARE: EXOTHERMIC REACTION) keeping the internal temperature below 80° C. The mixture was extracted with ether (3×) and the combined organic extracts were washed with brine, dried (magnesium sulfate) and concentrated in vacuo to leave the product (32 g, 94%) as an orange solid. A recrystallised sample (heptane, ethyl acetate) gave mp 80–82° C.;

$C_7H_7FN_2O_2$ requires: C, 49.42; H, 4.15; N, 16.46%. Found C, 49.60; H, 4.15; N, 16.57%.

3-Chloro-4-fluoro-6-methylnitrobenzene

A solution of sodium nitrite (7.6 g, 110 mmol) in water (20 mL) was added dropwise over 30 min at 0° C. to a stirred suspension of 2-fluoro-4-methyl-5-nitroaniline (17 g, 100 mmol) in concentrated hydrochloric acid (200 mL). The mixture was stirred at 0° C. for 20 min then transferred to a dropping funnel and added dropwise over 30 min to a stirred suspension of copper(I)chloride (16 g) in concentrated hydrochloric acid (150 mL) at 0° C. The mixture was allowed to warm to room temperature and stirred for 16 h then poured onto ice-water (1.5 L) and extracted with ethyl acetate (3×). The combined organic extracts were washed with brine, dried (magnesium sulfate), concentrated in vacuo and purified by column chromatography [$SiO_2$; heptane] to give the product (14.2 g, 75%) as a yellow solid. An analytical sample was recrystallised (heptane) to give a white solid: mp 57–58° C.; NMR $\delta_H$ (400 MHz, $CDCl_3$) 8.03 (1H, d, J 7.2 Hz), 7.13 (1H, d, J 9.1 Hz), 2.6 (3H, s).

6-Chloro-5-fluoro-1H-indole

N,N-Dimethylformamide dimethylacetal (6.3 ml, 45 mmol) was added in one portion to a stirred solution of 3-chloro-4-fluoro-6-methylnitrobenzene (7.0 g, 37 mmol) in N,N-dimethylformamide (30 mL) at 130° C. under Ar. The mixture was stirred at 130° C. for 2 h, cooled to room temperature, concentrated in vacuo and partitioned between ethyl acetate and water and the aqueous was extracted with ethyl acetate (2×). The combined organic extracts were washed with brine, dried (magnesium sulfate), concentrated in vacuo, dissolved in methanol/tetrahydrofuran (1:1; 100 mL) and Raney Nickel®, 50% wt. in water, (5 g) was added. The mixture was cooled to 0° C. and hydrazine hydrate (3 mL, 59 mmol) was added dropwise over 2 min. The mixture was warmed to room temperature, stirred for 1 h then cooled to 0° C. and hydrazine hydrate (1.5 mL) was added over 2 min. The mixture was warmed to room temperature, stirred for 1 h and filtered through celite®. The filter-cake was washed with tetrahydrofuran and the filtrate was concentrated in vacuo and purified by column chromatography [$SiO_2$; heptane-dichloromethane (4:1)] to give the product (3.2 g, 51%) as an off-white solid. An analytical sample was recrystallised (heptane) to give a white solid: mp 105–107° C.; NMR $\delta_H$ (400 MHz, $CDCl_3$) 8.01 (1H, br. s), 7.40 (1H, d, J 6 Hz), 7.35 (1H, d, J 9.4 Hz), 7.25 (1H, t, J 2.8 Hz), 6.50–6.51 (1H, m).

7-Chloro-5-fluoroindole

N-(2-Chloro-4-fluorophenyl)-2-(hydroxyimino)-acetamide

A solution of chloral hydrate (6.25 g, 37.8 mmol), sodium sulfate decahydrate (48.3 g, 340 mmol) and water (100 mL) was added to a stirred solution of 2-chloro-4-fluoroaniline (5.0 g, 34 mmol), hydroxylamine hydrochloride (9.19 g, 130 mmol), water (50 mL) and concentrated hydrochloric acid (3 mL). The reaction mixture was heated under reflux for 1 h, cooled to room temperature, stirred for 16 h and filtered. The filter-cake was recrystallised (methanol-water) to give the product (5.58 g, 75% yield) as a pale brown solid: IR $\nu_{max}$ (Nujol)/cm$^{-1}$ 1655, 1613, 1536, 1267, 1191, 1021, 853 and 558; NMR $\delta_H$ (400 MHz, DMSO-$d_6$) 7.20–7.29 (1H, m), 7.51–7.57 (1H, m), 7.78–7.84 (1H, m), 9.61 (1H, s) and 12.36 (1H, s).

7-Chloro-5-fluoroindole-2,3-dione

N-(2-Chloro-4-fluorophenyl)-2-(hydroxyimino)-acetamide (5.4 g, 24.9 mmol) was added portionwise to conc. sulfuric acid (70 mL) at 70° C. The mixture was stirred for 1 h, poured onto ice-water (200 mL) and filtered. The filter-cake was dried in vacuo to give crude 7-chloro-5-fluoroindole-2,3-dione which was used immediately without further purification.

7-Chloro-5-fluoroindole

To a stirred solution of lithium aluminium hydride (0.57 g, 15 mmol) in THF (20 mL) at 0° C. under Ar was added portionwise 7-chloro-5-fluoroindole-2,3-dione. The mixture was heated under reflux for 4 h, cooled to 0° C. and water (0.5 mL) was added. The mixture was stirred for 5 min then treated with aqueous sodium hydroxide solution (2 N, 0.5 mL) followed by water (0.5 mL) and filtered through a pad of celite®. The filter-cake was washed with tetrahydrofuran and the filtrate was concentrated in vacuo and purified by column chromatography [$SiO_2$; heptane-ethyl acetate (3:1)] to give the product (0.31 g, 37% yield) as a blue-oil: IR $\nu_{max}$ (film)/cm$^{-1}$ 3459, 1575, 1485, 1341, 1120 and 722; NMR $\delta_H$ (400 MHz, $CDCl_3$) 6.55 (1H, t, J 2.5 Hz) 7.01 (1H, dd, J 9,2 Hz) 7.21 (1H, m) 7.29 (1H, t, J 2.5 Hz) 8.33 (1H, brs).

6-Chloro-7-fluoroindole

Methyl 2-azido-3-(4-chloro-3-fluorophenyl)propenoate

Sodium (2.32 g, 100 mmol) was added portionwise to stirred methanol (200 mL) at 0° C. under Ar. The mixture was stirred for 1 h and cooled to −15° C. A solution of 4-chloro-3-fluorobenzaldehyde (4.0 g, 25 mmol), methyl azidoacetate (8.7 g, 75 mmol) in methanol (20 mL) was added. The mixture was stirred for 3 h, warmed to 4° C. and stirred for 16 h and partitioned between water (300 mL) and ether (3×200 mL). The organic extracts were combined and washed with brine (2×), dried (magnesium sulfate) and concentrated in vacuo to give an orange solid. Recrystallisation (methanol) gave the product (5.09 g, 80% yield) as a pale yellow solid: IR $\nu_{max}$ (Nujol)/cm$^{-1}$ 2115, 1708, 1616, 1234, 1060, 896, 818 and 616; NMR $\delta_H$ (400 MHz, $CDCl_3$) 3.82 (3H, s) 6.64 (1H, s) 7.35–7.46 (2H, m) 7.74–7.78 (1H, m).

Methyl 6-chloro-7-fluoroindole-2-carboxylate

A solution of methyl 2-azido-3-(4-chloro-3-fluorophenyl) propenoate (15.08 g, 59 mmol) in xylene (200 mL) was added dropwise to stirred xylene (1 L) under reflux. The mixture was stirred for 3 h, cooled to room temperature, concentrated in vacuo and purified by column chromatography [$SiO_2$; isopropyl ether-hexane (5:2)] to give the product (2.3 g, 17% yield) as a colourless solid: IR $\nu_{max}$ (Nujol)/cm$^{-1}$ 3298, 1709, 1460, 1377, 1204 and 737; NMR $\delta_H$ (400 MHz, $CDCl_3$) 3.85 (3H, s) 7.09–7.15 (1H, m) 7.21 (1H, m) 7.38 (1H, m) and 9.05 (1H, brs).

6-Chloro-7-fluoroindole-2-carboxylic Acid

A stirred solution of methyl 6-chloro-7-fluoroindole-2-carboxylate (2.3 g, 10 mmol), tetrahydrofuran (20 mL) and aqueous sodium hydroxide solution (2 N, 20 mL) was heated under reflux for 16 h. The mixture was cooled to room temperature and partitioned between aqueous sulfiuric acid (2 M, 30 mL) and ethyl acetate (3×30 mL). The combined organic extracts were dried (magnesium sulfate) and concentrated in vacuo to give the product (2.1 g, 98% yield) as a white solid: IR $\nu_{max}$ (Nujol)/cm$^{-1}$ 1681, 1557, 1263, 1206, 926 and 840; NMR $\delta_H$ (400 MHz, DMSO-$d_6$) 7.01–7.12 (2H, m) and 7.31–7.34 (1H, m).

6-Chloro-7-fluoroindole

A solution of 6-chloro-7-fluoroindole-2-carboxylic acid (2.1 g, 9.8 mmol) and diphenyl ether (30 mL) was heated under reflux for 4 h, cooled to room temperature and purified by column chromatography [$SiO_2$; heptane-ethyl acetate (99:1 to 10:1)] to give the product (1.04 g, 63% yield) as a pale brown oil: IR $\nu_{max}$ (Nujol)/cm$^{-1}$ 3460, 1573, 1490, 1446, 1201, 802 and 619; NMR $\delta_H$ (400 MHz, $CDCl_3$) 6.44 (1H, brs) 7.04–7.09 (1H, m) 7.21–7.26 (1H, m) 7.30–7.34 (1H, m) and 8.40 (1H, brs).

6-Bromo-5-fluoroindole
3-Bromo-4-fluoro-6-methylnitrobenzene

A solution of sodium nitrite (7.6 g, 110 mmol) in water (30 mL) was added dropwise over 15 min to a stirred suspension of 2-fluoro-4-methyl-5-nitroaniline (17 g, 100 mmol) in hydrobromic acid, (48%, 150 mL) and water (30 mL) at 0° C. The mixture was stirred at 0° C. for 15 min then added portionwise over 10 min to a stirred suspension of copper(I)bromide (16.5 g, 112 mmol) in hydrobromic acid (48%, 50 mL) and water (90 mL) at 0° C. The mixture was stirred at 0° C. for 30 min then warmed to room temperature and stirred for 3 h. The mixture was poured onto ice-water (500 mL) and extracted with ethyl acetate (3x). The combined organic extracts were washed with saturated aqueous sodium bicarbonate solution, dried (magnesium sulfate), concentrated in vacuo and purified by column chromatography [$SiO_2$; heptane-ethyl acetate (19:1)] to give the product (11.8 g, 50%) as an off-white solid: IR $v_{max}$ (nujol)/cm$^{-1}$ 2925, 2855, 1571, 1523, 1478, 1349, 1264, 1103, 895, 671 and 589; NMR $\delta_H$ (400 MHz, CDCl$_3$) 8.27 (1H, d, J 6.5), 7.10 (1H, d, J 9.1), 2.60 (3H, s).

6-Bromo-5-fluoroindole

N,N-Dimethylformamide dimethylacetal (8.5 mL, 60 mmol) was added in one portion to a stirred solution of 3-bromo-4-fluoro-6-methylnitrobenzene (11.8 g, 50 mmol) in N,N-dimethylformamide (30 mL) at room temperature under Ar. The mixture was heated to 120° C., stirred for 16 h then concentrated in vacuo to leave a crude oil. The oil was crystallised [methanol-dichloromethane (4:1)] to give a purple solid (4.5 g). The solid was dissolved in methanol/tetrahydrofuran (1:1; 30 mL) and Raney Nickel® (1 g) was added. The mixture was cooled to 0° C. and hydrazine hydrate (0.8 mL, 16 mmol) was added in one portion. The mixture was stirred at 0° C. for 90 min then a further aliquot of hydrazine hydrate (0.8 mL) was added. The mixture was stirred at 0° C. for 30 min then filtered through celite® and the filter cake was washed with tetrahydrofuran. The filtrate was concentrated in vacuo and purified by column chromatography [$SiO_2$; heptane-dichloromethane (4:1)] to give the product (1.7 g, 16%) as an off-white solid: IR $v_{max}$ (nujol)/cm$^{-1}$ 3395, 2925, 2855, 1570, 1469, 1451, 1408, 1314, 1145, 1105, 865, 763 and 502; NMR $\delta_H$ (400 MHz, CDCl$_3$) 7.85 (1H, br. s), 7.55 (1H, d, J 5.5 Hz), 7.34 (1H, d, J 9 Hz), 7.23 (1H, t, J 2.8 Hz), 6.49–6.51 (1H, m).

5-Fluoro-6-methylthioindole
5-Fluoro-6-methylthioindole-2,3-dione

Sodium thiomethoxide (5.93 g, 84.6 mmol) was added to a solution of 5,6-difluoroindole-2,3-dione (7.75 g, 42.3 mmol) in dimethylformamide (400 mL). The reaction was stirred at room temperature for 1 h, then poured onto ice (2 L). The resulting solid was collected by filtration, washed with water and dried at 40° C. under vacuum to give a brown solid (3.12 g, 35%): mp 296° C.; C$_9$H$_6$F$_1$NO$_2$S requires: C, 51.18; H, 2.86; N, 6.63; S, 15.18%. Found C, 50.95; H, 2.85; N, 6.58; S, 15.35%; IR $v_{max}$ (Nujol)/cm$^{-1}$ 3285, 2925, 2854, 1760, 1714, 1611, 1465 and 1036; NMR $\delta_H$ (400 MHz, DMSO-d$_6$) 2.58 (3H, s), 6.71 (1H, d, J 6.0 Hz), 7.38 (1H, d, J 9.0 Hz), 11.02 (1H, brs).

5-Fluoro-6-methylthioindole

5-Fluoro-6-methylthioindole was prepared from 5-fluoro-6-methylthioindole-2,3-dione according to the method described in the preparation of 7-chloro-5-fluoroindole as a white solid (1.21 g, 37%): mp 51° C.; C$_9$H$_8$FNS requires: C, 59.65; H, 4.45; N, 7.73; S, 17.69%. Found C, 59.75; H, 4.44; N, 7.72; S, 17.65%; IR $\delta_{max}$ (Nujol)/cm$^{-1}$ 3461, 3408, 3361, 2925, 2855, 1455, 1304 and 1137; NMR $\delta_H$ (400 MHz, CDCl$_3$) 2.49 (3H, s), 6.49–6.51 (1H, m), 7.22 (1H, t, J 3.0 Hz), 7.30 (1H, d, J 10.0 Hz), 7.36 (1H, d, J 6.5 Hz), 8.0–8.25 (1H, brm).

6-Ethylthio-5-fluoroindole
6-Ethylthio-5-fluoroindole-2,3-dione

6-Ethylthio-5-fluoroindole-2,3-dione was prepared from 5,6-difluoroindole-2,3-dione using sodium thioethoxide according to the method described in the synthesis of 5-fluoro-6-methylthioindole as a brown solid (2.53 g, 19%): mp 215° C.; IR $v_{max}$ (Nujol)/cm$^{-1}$ 3286, 2926, 2855, 1766, 1712, 1619, 1467 and 1038; NMR $\delta_H$(400 MHz, DMSO-d$_6$) 1.32 (3H, t, J 7.5 Hz), 3.13 (2H, q, J 7.5 Hz), 6.77 (1H, d, J 6.0 Hz), 7.39 (1H, d, J 8.5 Hz), 10.97 (1H, brs).

6-Ethylthio-5-fluoroindole

6-Ethylthio-5-fluoroindole was prepared from 6-ethylthio-5-fluoroindole-2,3-dione according to the method described in the synthesis of 7-chloro-5-fluoroindole as a pale green oil (0.49 g, 23%): IR $v_{max}$ (film)/cm$^{-1}$ 3426, 2969, 2927, 1565, 1471, 1454, 1307, 1140 and 1101; NMR $\delta_H$ (400 MHz, CDCl$_3$) 1.26 (3H, t, J 7.5), 2.91 (2H, q, J 7.5 Hz), 6.48–6.51 (1H, m), 7.23 (1H, t, J 2.5 Hz), 7.31 (1H, d, J 10.0 Hz), 7.46 (1H, d, J 6.0 Hz), 8.01–8.25 (1H, brm).

6-Methylthioindole

To a stirred suspension of potassium hydride (30% dispersion in mineral oil, 0.68 g, 5.10 mmol) in dry tetrahydrofuran (20 mL) at 0° C., under Ar, was added a solution of 6-bromoindole (1.0 g, 5.1 mmol) in tetrahydrofuran (10 mL). After 15 mins, the solution was cooled to −78° C. and tert-butyllithium (1.7 M, 6.0 mL, 10 mmol) was added dropwise. The mixture was stirred for a further 15 mins and then dimethyl disulphide (0.92 mL, 10.2 mmol) was added dropwise. The solution was warmned gradually to room temperature, then diluted carefully with saturated ammonium chloride solution (20 mL). The mixture was extracted with ether (2x50 mL). The combined organic extracts were dried (magnesium sulfate), concentrated in vacuo and purified by column chromatography [$SiO_2$; heptane-dichloromethane (1:1)] to give the product as a pale-yellow solid (0.56 g, 68%): mp. 91–92° C.; NMR $\delta_H$ (400 MHz, CDCl$_3$) 2.51 (3H, s), 6.49 (1H, m), 7.09–7.16 (2H, m), 7.35 (1H, s), 7.54 (1H, d, J 8.2 Hz) and 8.09 (1H, br s); IR (Nujol)$v_{max}$/cm$^{-1}$ 3388, 2925, 1459, 1311, 1098, 810, 717 and 527.

6-Ethylthioindole

6-Ethylthioindole was prepared according to the method described for the synthesis of 6-methylthioindole as a clear oil (0.73 g, 81%). NMR $\delta_H$ (400 MHz, CDCl$_3$) 1.27 (3H, t, J 7.6 Hz), 2.93 (2H, q, J 7.5 Hz), 6.51 (1H, m), 7.16–7.18 (2H, m), 7.45 (1H, s), 7.55 (1H, d, J 8.3 Hz) and 8.10 (1H, br s); IR (film)$v_{max}$/cm$^{-1}$ 3404, 2970, 1616, 1450, 1310, 810 and 723.

6-n-Propylthioindole 6-n-Propylthioindole was prepared according to the method described for the synthesis of 6-methylthioindole as a clear oil, which solidified on standing (0.88 g, 91%). mp. 54–55° C.; NMR $\delta_H$ (400 MHz, CDCl$_3$) 0.99 (3H, t, J 7.4 Hz), 1.56–1.65 (2H, m), 2.87 (2H, dd, J 14.5, 7.1 Hz), 6.51 (1H, m), 7.16–7.18 (2H, m), 7.45 (1H, s), 7.54 (1H, d, J 8.0 Hz), and 8.10 (1H, br s); IR (Nujol)$v_{max}$/cm$^{-1}$ 3388, 2924, 1614, 1452, 1311, 810, 718 and 524.

6-Isopropylthioindole

6-Isopropylthioindole was prepared according to the method described for the synthesis of 6-methylthioindole as a clear, viscous oil (0.59 g, 61%). NMR $\delta_H$ (400 MHz, CDCl$_3$) 1.26 (6H, d, J 7.0 Hz), 3.25–3.32 (1H, m), 6.52 (1H, m), 7.19–7.56 (2H, m) and 8.12 (1H, br s); IR (Nujol)$v_{max}$/cm$^{-1}$ 3416, 2960, 1613, 1449, 1338, 1050, 810 and 606.

General Method C

Example 43
(S)-1-(6-Phenylindolin-1-yl)-2-propylamine Fumarate

Step a: (S)-1-[2-(tert-Butoxycarbonylamino)propyl]-6-phenylindoline (43a)

To a stirred solution of palladium(II)acetate (0.011 g, 0.05 mmol) and triphenylphosphine (0.052 g, 0.2 mmol) in tetrahydrofuran (5 mL) under Ar was added (S)-1-[2-(tert-butoxycarbonylamino)propyl]-6-bromoindoline (0.34 g, 1 mmol). The mixture was stirred for 10 min and treated with a solution of phenyl boronic acid (0.24 g, 2 mmol) in ethanol (2 mL) followed by aqueous sodium bicarbonate solution (2 M, 5 mL). The mixture was heated under reflux for 2 h and cooled to room temperature. The mixture was partitioned between ether (50 mL) and water (2×20 mL). The organic layer was dried (magnesium sulfate), concentrated in vacuo and purified by column chromatography [SiO$_2$; heptane-ethyl acetate (6:1)] to give the product (0.24 g, 69% yield) as a colourless oil. Data for (43a) are included in Table 10 with the compounds prepared using General Method C, step (a).

Step (b): (S)-1-(6-Phenylindolin-1-yl)-2-propylamine Fumarate (43)

(S)-1-(6-Phenylindolin-1-yl)-2-propylamine fumarate was prepared according to the method described in General Method B, step (c) using (S)-1-[2-(tert-butoxycarbonylamino)propyl]-6-phenylindoline to give the product (0.12 g, 65% yield) as a white solid. Data for (43) are included in Table 11 with the compounds prepared using General Method C, step (b).

The compounds shown in Tables 10 and 11 were prepared according to General Method C using the appropriate aryl boronic acid.

TABLE 10

Indolines prepared using General Method C, step (a)

| No | Ar | Data |
|---|---|---|
| 43a | Ph | IR $v_{max}$ (Nujol)/cm$^{-1}$ 1682, 1529, 1456, 1367, 1170, 1064 and 756; NMR $\delta_H$ (400 MHz, CDCl$_3$) 1.23 (3H, d, J 6 Hz), 1.41 (9H, s), 3.06 (1H, t, J 8.5 Hz), 3.14 (1H, d, J 6.5 Hz), 3.46–3.56 (2H, m), 3.94 (1H, m), 4.56 (1H, brs), 6.68 (1H, brs), 6.88 (1H, dd, J 8, 1.5 Hz), 7.13 (1H, d, J 7.5 Hz), 7.29–7.34 (1H, m), 7.38–7.43 (1H, m) and 7.54–7.58 (1H, m). |
| 44a | 4-Cl—C$_6$H$_4$ | IR $v_{max}$ (Nujol)/cm$^{-1}$ 1691, 1459, 1377, 1171, 1055, 832, and 801; NMR $\delta_H$ (400 MHz, CDCl$_3$) 1.14 (3H, d, J 6.5 Hz) 1.45 (9H, s) 4.02–4.49 (7H, m) 6.51 (1H, d, J 3 Hz) 7.06–7.12 (2H, m) 7.42 (1H, brs) 7.54 (1H, d, J 9 Hz). |
| 45a | 4-F—C$_6$H$_4$ | IR $v_{max}$ (Nujol)/cm$^{-1}$ 1679, 1530, 1168, 1064, 838 and 805; NMR $\delta_H$ (400 MHz, CDCl$_3$) 1.27 (3H, d, J 6 Hz), 1.41 (9H, s), 3.0–3.15 (3H, m), 3.95 (1H, brs), 6.63 (1H, brs), 6.81–6.85 (1H, m), 7.05–7.13 (3H, m), and 7.50–7.53 (2H, m). |
| 46a | 4-OMe—C$_6$H$_4$ | IR $v_{max}$ (Nujol)/cm$^{-1}$ 1694, 1609, 1518, 1365, 1245, 1177, 833 and 804; NMR $\delta_H$ (400 MHz, CDCl$_3$) 1.25 (3H, d, J 6 Hz), 1.41 (9H, s), 2.98–3.03 (1H, m), 3.1–3.13 (1H, m), 3.42–3.53 (2H, m), 3.84 (3H, s), 4.58 (1H, brs), 6.63 (1H, brs), 6.82–6.85 (1H, m), 6.94 (2H, d, J 8.5 Hz), 7.09 (1H, d J) 7 Hz) and 7.49 (2H, d, J 8.5 Hz). |
| 47a | 3-pyridinyl | IR $v_{max}$ (Nujol)/cm$^{-1}$ 1690, 1526, 1458, 1176, 1053 and 788; NMR $\delta_H$ (400 MHz, CDCl$_3$) 1.28 (3H, d, J 6.5 Hz), 1.43 (9H, s), 3.07 (1H, t, J 8.5 Hz), 3.14–3.20 (2H, m), 3.49–3.62 (2H, m), 3.95–4.01 (1H, m), 4.57 (1H, brs), 6.66 (1H, brs), 7.84 (1H, d, J 7 Hz), 7.18 (1H, d, J 7 Hz), 7.35–7.39 (1H, m), 7.90 (1H, dt, J 7.5, 1.5 Hz), 8.59–8.64 (1H, m) and 8.85 (1H, brs). |
| 48a | 3-thiophenyl | IR $v_{max}$ (Nujol)/cm$^{-1}$ 1686, 1514, 1357, 1172, 1080 and 775; NMR $\delta_H$ (400 MHz, CDCl$_3$) 1.28 (3H, d, J 6 Hz), 1.45 (9H, s), 3.03 (2H, t, J 8.5 Hz), 3.12–3.16 (2H, m), 3.44–3.50 (2H, m), 3.93–4.0 (1H, m), 4.59 (1H, brs), 6.73 (1H, brs), 6.29 (1H, dd, J 7, 1.5 Hz) 7.11 (1H, d, J 7 Hz), 7.36–7.38 (2H, m) and 7.41–7.43 (1H, m). |

TABLE 11

Examples 43–48. Indolines prepared using General Method C, step (b)

| No | Ar | Data |
|---|---|---|
| 43 | Ph | Fumarate. mp 153–154° C.; NMR $\delta_H$ (400 MHz, DMSO-$d_6$) 1.23 (3H, d, J 6 Hz), 2.90–2.98 (2H, m), 3.06 (1H, dd, J 13, 5 Hz), 3.23–3.45 (2H, m), 3.50–3.56 (2H, m), 6.84 (1H, d, J 1.5 Hz), 6.87 (1H, dd, J 7.5, 1.5 Hz), 7.11 (1H, d, J 7.5 Hz), 7.28–7.33 (2H, m), 7.38–7.43 (1H, m) and 7.58–7.62 (1H, m). |
| 44 | 4-Cl—$C_6H_4$ | Fumarate. mp 171–173° C.; NMR $\delta_H$ (400 MHz, DMSO-$d_6$) 1.26 (3H, d, J 6.5 Hz), 2.93–2.99 (2H, m), 3.07–3.13 (2H, m), 3.29–3.49 (2H, m), 3.521–3.60 (1H, m), 6.88–6.91 (2H, m), 7.13 (1H, d, J 7 Hz), 7.48 (2H, d, J 9 Hz) and 7.67 (2H, d, J 9 Hz). |
| 45 | 4-F—$C_6H_4$ | Fumarate. mp 148–149° C.; NMR $\delta_H$ (400 MHz, DMSO-$d_6$) 1.23 (3H, d, J 6 Hz), 3.05 (1H, dd, J 13, 5 Hz), 3.27–3.56 (6H, m), 6.80–6.86 (2H, m), 7.09 (1H, d J 6.5 Hz), 7.23 (2H, t, J 8 Hz) and 7.60–7.66 (2H, m). |
| 46 | 4-OMe—$C_6H_4$ | Fumarate. mp 174–176° C.; NMR $\delta_H$ (400 MHz, DMSO-$d_6$) 1.19 (3H, d, J 6.5 Hz), 2.87–2.95 (2H, m), 3.18–3.57 (5H, m), 3.79 (3H, s), 6.78 (1H, brs), 6.82 (1H, dd, J 7, 1 Hz), 6.99 (2H, d, J 8.5 Hz), 7.08 (1H, d, J 8 Hz) and 7.55 (2H, d, J 8.5 Hz). |
| 47 | 3-pyridinyl | Fumarate. mp 155° C. (dec.); NMR $\delta_H$ (400 MHz, DMSO-$d_6$) 1.27 (3H, d, J 6 Hz), 2.93–3.02 (2H, m), 3.12 (1H, dd, J 13, 4.5 Hz), 3.32–3.60 (4H, m), 6.93–6.96 (1H, m), 7.17 (1H, d, J 8 Hz), 7.43–7.47 (1H, m), 8.01–8.06 (1H, m), 8.52–8.55 (1H, m) and 8.86–8.88 (1H, brs). |
| 48 | 3-thiophenyl | Fumarate. mp 182–186° C.; NMR $\delta_H$ (400 MHz, DMSO-$d_6$) 1.27 (3H, d, J 6 Hz), 2.91–2.99 (2H, m), 3.09 (1H, dd, J 13), 5.5 Hz), 3.28–3.58 (5H, m), 6.94–6.98 (1H, m), 7.08 (1H, d, J 8 Hz), 7.59 (1H, dd, J 5, 3 Hz), 7.53 (1H, dd, J 5, 1.5 Hz) and 7.78–7.80 (1H, m). |

Example 49
(S)-1-[6-(4-Morpholinyl)indolin-1-yl]-2-propylamine Fumarate

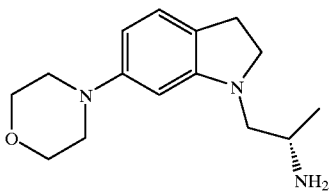

(S)-1-[2-(tert-Butoxycarbonylamino)propyl]-6-(4-morpholinyl)indoline

A mixture of palladium(II)acetate (0.004 g, 0.016 mmol), BINAP (0.01 g, 0.016 mmol), cesium carbonate (0.15 g, 0.45 mmol), toluene (2 mL), (S)-1-[2-(tert-butoxycarbonylamino)propyl-6-bromoindoline (0.11 g, 0.32 mmol) and morpholine (0.04 mL, 0.38 mmol) under argon was heated at 100° C. for 16 h, concentrated in vacuo and purified by column chromatography [SiO$_2$; isopropyl ether-heptane (1:1)] to give the product (0.05 g, 45% yield) as a pale yellow oil: IR $\nu_{max}$ (Nujol)/cm$^{-1}$ 1678, 1615, 1522, 1459, 810 and 767; NMR $\delta_H$ (400 MHz, CDCl$_3$) 1.26 (3H, d, J 6 Hz), 1.47 (9H, s), 2.94 (1H, t, J 7 Hz), 3.06 (1H, dd, J 10, 5 Hz), 3.11–3.18 (4H, m), 3.37–3.55 (2H, m), 3.82–3.95(5H, m), 4.60 (1H, brs), 6.17–6.26 (2H, m) and 6.99 (1H, d, J 7.5 Hz).

(S)-1-[6-(4-Morpholinyl)indolin-1-yl]-2-propylamine Fumarate (S)-1-[6-(4-Morpholinyl)indolin-1-yl]-2-propylamine fumarate was prepared according to the method in Example 10 using (S)-1-[2-(tert-butoxycarbonylamino) propyl]-6-(4-morpholinyl)indoline to give the product (0.02 g, 43%) as a beige solid: mp 188–191° C. (dec); IR $\nu_{max}$ (Nujol)/cm$^{-1}$ 1744, 1649, 1576, 1457, 1309, 1175, 984, 784 and 643.

Example 50
2-(6-Bromoindolin-1-yl)-1-ethylamine Fumarate

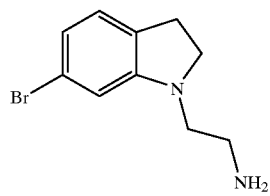

2-(6-Bromoindol-1-yl)-1-ethylamine Fumarate

To a stirred mixture of powdered sodium hydroxide (0.41 g, 10.2 mmol), tetrabutylammonium hydrogensulfate (0.034 g, 0.1 mmol), 6-bromoindole (0.5 g, 2.5 mmol) and acetonitrile (15 mL) was added 2-chloroethylamine hydrochloride (0.31 g, 2.75 mmol). The mixture heated under reflux for 16 h and partitioned between water (30 mL) and ether (2×30 mL). The combined organic extracts were washed with brine (2×), dried (magnesium sulfate), concentrated in vacuo and purified by column chromatography [SiO$_2$; ethyl acetate-methanol-0.880 ammonia solution (90:9:1)] to give a pale brown oil. The oil was dissolved in 2-propanol (10 mL) and the solution was heated to reflux, fumaric acid (0.29 g, 2.5 mmol) was added and the mixture was cooled to room temperature and filtered. The filter-cake was dried in vacuo to give the product (0.72 g, 81% yield) as a white solid: mp 214–216° C.; NMR $\delta_H$ (400 MHz, DMSO-d$_6$) 3.08 (2H, t, J 8 Hz), 4.33(2H, t, J 8 Hz), 6.47–6.52 (1H, m), 7.14–7.19 (1H, m), 7.41–7.44 (1H, m), 7.52 (1H, d, J 6.5 Hz) and 7.82 (1H, brs).

1-[2-(tert-Butoxycarbonylamino)ethyl]-6-bromoindole

To a stirred mixture of 2-(6-bromoindol-1-yl)-1-ethylamine fumarate (1.4 mmol), tert-butanol (3 mL), water (3 mL) and powdered sodium hydroxide (0.22 g, 5.5 mmol) was addded di-tert-butyl-dicarbonate (0.3 g, 1.4 mmol). The mixture was stirred for 16 h and partitioned between water (20 mL) and ethyl acetate (2×30 mL). The organic extracts were combined, washed with brine (2×), dried (magnesium sulfate), concentrated in vacuo and purified by column chromatography [SiO$_2$; heptane-ethyl acetate (5:1)] to give the product (0.25 g, 53% yield) as a white solid: IR $v_{max}$ (Nujol)/cm$^{-1}$ 1683, 1528, 1459, 1303, 1164, 1060 and 717; NMR $\delta_H$ (400 MHz, CDCl$_3$) 1.44 (9H, s), 3.45–3.51 (2H, m), 4.25–4.30 (2H, m), 4.53 (1H, brs), 6.73 (1H, d, J 3 Hz), 7.05 (1H, d, J 3 Hz), 7.20 (1H, dd, J 7.5, 2 Hz) and 7.50 (1H, d, J 7.5 Hz).

1-[2-(tert-Butoxycarbonylamino)ethyl]-6-bromoindoline

1-[2-(tert-Butoxycarbonylamino)ethyl]-6-bromoindoline was prepared according to General Method B, step (b) using 1-[2-(tert-butoxycarbonylamino)ethyl]-6-bromoindole to give the product 0.19 g (93% yield) as a white solid: IR $v_{max}$ (Nujol)/cm$^{-1}$ 1684, 1603, 1532, 1302,984 and 781; NMR $\delta_H$ (400 MHz, CDCl$_3$) 1.46 (9H, s) 2.92 (2H, t, J 8 Hz) 3.17 (2H, t, J 6 Hz) 3.31–3.36 (1H, m) 3.4 (2H, t, J 8 hz) 4.78 (1H, brs) 6.57 (1H, brs) 6.75 (1H, dd, J 7.5, 2 Hz) and 6.90–6.95 (1H, m).

2-(6-Bromoindolin-1-yl)-1-ethylamine Fumarate 2-(6-Bromoindolin-1-yl)-1-ethylamine fumarate was prepared according to General Method B, step (c) using 1-[2-(tert-butoxycarbonylamino)ethyl]-6-bromoindole to give the product 0.14 g (73% yield) as a white solid: mp 203–206° C.; NMR $\delta_H$ (400 MHz, DMSO-d$_6$) 2.80–2.90 (2H, m) 3.14–3.17 (2H, m) 3.35–3.41 (4H, m) 6.64–6.69 (2H, m) and 6.93 (1H, d, J 8 Hz).

Example 51
2-(6-Chloroindolin-1-yl)-1-ethylamine Fumarate

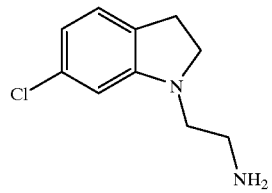

2-(6-Chloroindol-1-yl)-1-ethylamine Fumarate 2-(6-Chloroindol-1-yl)-1-ethylamine fumarate was prepared according to the method described in Example 50 using 6-chloroindole to give the product (1.34 g, 64% yield) as a colourless solid: mp. 210–213° C.; NMR $\delta_H$ (400 MHz, CDCl$_3$) 3.01 (2H, t, J 6.5 Hz), 4.26 (2H, t, J 6.5 Hz), 6.46–6.48 (2H, m), 7.02 (1H, dd, J 8, 1.5), 7.41 (1H, d, J 3 Hz) 7.54 (1H, d, J 8 Hz) and 7.65–7.66 (1H, m).

1-[2-(tert-Butoxycarbonylamino]ethyl)-6-chloroindole

1-[2-(tert-Butoxycarbonylamino]ethyl)-6-chloroindole was prepared according to the method described in Example 50 using 2-(6-chloroindol-1-yl)-1-ethylamine fumarate to give the product (1.02 g, 86% yield) as a white solid: IR $v_{max}$ (Nujol)/cm$^{-1}$ 1686, 1611, 1538, 1467, 1279, 1143, 796 and 718; NMR $\delta_H$ (400 MHz, CDCl$_3$) 1.45 (9H, s), 3.45–3.51 (2H, m), 4.21–4.27 (2H, m), 4.54 (1H, brs), 6.49 (1H, brs), 7.05–7.09 (2H, m), 7.34 (1H, s) and 7.53 (1H, d, J 8.5 Hz).

1-[2-(tert-Butoxycarbonylamino]ethyl)-6-chloroindoline

1-[2-(tert-Butoxycarbonylamino]ethyl)-6-chloroindoline was prepared according to General method B, step (b) using 1-[2-(tert-butoxycarbonylamino]ethyl)-6-chloroindole to give the product 0.75 g (75% yield) as a colourless solid: IR $v_{max}$ (Nujol)/cm$^{-1}$ 1684, 1606, 1533, 1362, 1165 and 782; NMR $\delta_H$ (400 MHz, CDCl$_3$) 1.43 (9H, s), 2.92 (2H, t, J 8 Hz), 3.15 (2H, t, J 6 Hz), 3.28–3.35 (1H, m), 3.40 (2H, t, J 8 Hz), 4.76 (1H, brs), 6.38–6.40 (1H, s), 6.56–6.59 (1H, m) and 6.90–6.93 (1H, m).

2-(6-Chloroindolin-1-yl)-1-ethylamine Fumarate 2-(6-Chloroindolin-1-yl)-1-ethylamine fumarate was prepared according to General Method B, step (c) using 1-[2-(tert-butoxycarbonylamino]ethyl)-6-chloroindoline to give the product 0.39 g (55% yield) as a white solid: mp 195–196° C.; NMR $\delta_H$ (400 MHz, DMSO d$_6$) 2.88 (2H, t, J 8.5 Hz), 2.98 (2H, t, J 6 Hz), 3.28 (2H, t, J 6 Hz), 3.41 (2H, t, J 8.5 Hz), 6.55–6.59 (2H, m) and 6.99 (1H, d, J 7.5 Hz).

Example 52

N,N-Dimethyl-2-(6-Chloroindolin-1-yl)-1-ethylamine Fumarate

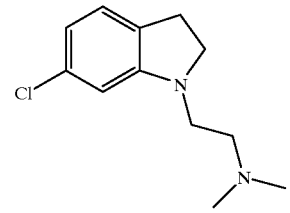

N,N-Dimethyl-2-(6-chloroindol-1-yl)-1-ethylamine Fumarate

N,N-Dimethyl-2-(6-chloroindol-1-yl)-1-ethylamine fumarate was prepared according to the method described in Example 50 using 6-chloroindole and 1-chloro-2-(dimethylamino)ethane to give the product (0.5 g, 22% yield) as a white solid: mp 163–165° C.; NMR $\delta_H$ (400 MHz, CDCl$_3$) 2.93 (6H, s), 3.37 (2H, t, J 6.5 Hz), 4.95 (2H, t, J 6.5 Hz), 7.13 (1H, d, J 3Hz), 7.68–7.72 (1H, m), 8.11 (1H, d, J 3 Hz), 8.22 (1H, d, J 8 Hz) and 8.29–8.31 (1H, m).

N,N-Dimethyl-2-(6-chloroindolin-1-yl)-1-ethylamine Fumarate

N,N-Dimethyl-2-(6-chloroindolin-1-yl)-1-ethylamine fumarate was prepared according to General Method B, step (b) using N,N-dimethy-2-(6-chloroindol-1-yl)-1-ethylamine fumarate to give the product 0.19 g (27% yield) as a colourless solid: mp 144–146° C.; NMR $\delta_H$ (400 MHz, DMSO-d$_6$) 2.41 (6H, s), 2.72 (2H, t, J 7 Hz), 2.88 (2H, t, J 8 Hz), 3.27 (2H, t, J 7 Hz), 3.43 (2H, t, J 8 Hz), 6.55 (1H, dd, J 7.5, 2.5 Hz), 6.58 (1H, brs) and 6.99 (1H, d, J 7.5 Hz).

Example 53

2-(6-Nitroindolin-1-yl)-1-ethylamine Fumarate

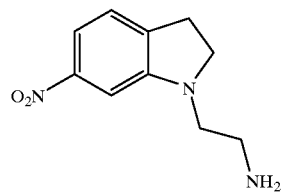

1-(6-Nitroindolin-1-yl)-acetonitrile

A stirred mixture of 6-nitroindoline (2.0 g, 12 mmol), potassium carbonate (3.36 g, 24 mmol), sodium iodide (3.65 g, 24.4 mmol), acetone (20 mL) and chloroacetonitrile (1.5 mL, 24 mmol) was heated under reflux for 16 h. The mixture was cooled to room temperature, filtered and the filter-cake washed with ethyl acetate. The filtrate was concentrated in vacuo and purified by column chromatography [$SiO_2$; heptane-ethyl acetate (9:1)] to give the product (1.3 g, 53% yield) as a pale yellow solid: IR $v_{max}$ (Nujol)/cm$^{-1}$ 1615, 1513, 1487, 1343, 1293, 1145, 804 and 739; NMR $\delta_H$ (400 MHz, CDCl$_3$) 3.11 (2H, t, J 7.5 Hz), 3.59 (2H, t, J 7.5 Hz), 4.14 (2H, s), 7.19–7.23 (1H, m), 7.31–7.33 (1H, m) and 7.69–7.72 (1H, m).

2-(6-Nitroindolin-1-yl)-1-ethylamine Fumarate

Borane-dimethylsulfide complex (0.25 mL, 2.6 mmol) was added dropwise to a stirred solution of 1-(6-nitroindolin-1-yl)-acetonitrile (0.38 g, 1.9 mmol) in tetrahydrofuran (10 mL) under Ar. The mixture was heated under reflux for 4 h then cooled to room temperature and stirred for 16 h. The mixture was cooled to 0° C., hydrochloric acid (3 M, 10 mL) was added and the mixture was heated under reflux for 1 h. The mixture was cooled to room temperature and washed with ethyl acetate (2×10 mL). The aqueous layer was partitioned between aqueous sodium hydroxide solution (2 M, 20 mL) and dichloromethane (3×30 mL). The combined dichloromethane extracts were dried (magnesium sulfate) and concentrated in vacuo to give a pale yellow oil. The oil was dissolved in 2-propanol (3 mL) and the solution was heated to reflux then fumaric acid (0.1 g, 0.87 mmol) was added. The mixture was cooled to room temperature and filtered. The filter-cake was dried in vacuo to give the product (0.36 g, 59% yield) as a white solid: mp 197° C. (dec.); NMR $\delta_H$ (400 MHz, DMSO-d$_6$) 2.99 (2H, t, J 7 Hz), 3.09 (2H, t, J 7 Hz), 3.38 (2H, t, J 7.5 Hz), 3.54 (2H, t, J 8.5 Hz), 6.44 (2H, s), 7.23–7.27 (2H, m) and 7.48 (1H, dd, J 8, 2 Hz).

Example 54

(S) N-(2-thiophenyl)methyl-1-(6-bromoindolin-1-yl)-2-propylamine Hydrochloride

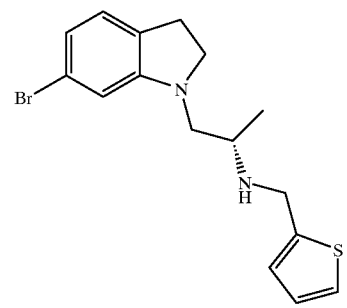

A mixture of (S)-(6-bromoindolin-1-yl)-2-propylamine (0.039 g, 0.15 mmol), thiophene-2-carboxaldehyde (0.034 g, 0.30 mmol) and methanol (1 mL) was shaken for 3 h. To the mixture was added Amberlite IRA-400 borohydride resin (2.5 mmol/g —BH$_4$, 0.12 g, 0.3 mmol) and the mixture was shaken for 18 h. To the mixture was added PS-benzaldehyde (2.5 mmol/g —CHO, 0.12 g, 0.3 mmol) and the mixture was shaken for 18 h and filtered. The filter-cake was washed with dichloromethane (2×1 mL) and methanol (2×1 mL) and the filtrate was concentrated in vacuo. The concentrate was dissolved in dichloromethane (2 mL) and Amberlyst-15 (0.5 g) was added. The mixture was shaken for 1 h and filtered. The filter-cake was washed with dichloromethane (2×1 mL) and methanol (2×1 mL), suspended in methanolic ammonia solution (2 M, 1 mL, 2 mmol), shaken for 1 h, and filtered. The fiter-cake was washed (dichloromethane) and the filtrate was concentrated in vacuo. The residue was treated with ethereal hydrogen chloride solution (1 M, 1 mL, 1 mmol) and concentrated in vacuo to give the product as a beige solid (0.037 g, 63%): mp 151–154° C.; NMR $\delta_H$ (400 MHz, DMSO-d$_6$) 1.37 (3H, d, J 6.5 Hz) 2.92 (2H, m) 3.15 (1H, dd, J 6,14 Hz) 3.31 (1H, q, J 9 Hz) 3.46 (2H, m) 3.55 (1H, m) 4.47 (2H, m) 6.79 (1H, d, J 7.5 Hz) 6.80 (1H, s) 6.99 (1H, d, J 8 Hz) 7.13 (1H, m) 7.41 (1H, d, J 2.5 Hz) 7.66 (1H, d, J 5 Hz).

The compounds shown in Table 12 were prepared from (S)-(6-bromoindolin-1-yl)-2-propylamine and the appropriate aldehyde according to the method described in Example 54.

TABLE 12

Examples 55–59. Indolines prepared according to the method described in Example 54.

| No | Structure | Data |
|---|---|---|
| 55 | Chiral (structure shown) | HCl. mp 155–156° C.; NMR $\delta_H$ (400 MHz, DMSO-d$_6$) 0.38 (2H, dd, J 2, 4.5 Hz), 0.57(2H, t, J 7.5 Hz), 1.12(1H, m), 1.28(3H, d, J 6.5 Hz), 2.81(1H, m), 2.90(2H, t, J 8 Hz), 2.92(1H, m), 3.16(1H, m), 3.35(1H, q, J 8.5 Hz), 3.50 (3H, m), 6.73(1H, dd, J 1.5, 7.5 Hz), 6.80(1H, d, J 1.5 Hz), 6.97(1H, d, J 7.5 Hz). |

TABLE 12-continued

Examples 55–59. Indolines prepared according to the method described in Example 54.

| No | Structure | Data |
| --- | --- | --- |
| 56 | 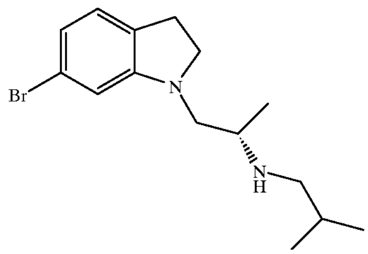 | HCl. mp 151–153° C.; NMR δ$_H$ (400 MHz, DMSO-d$_6$) 0.98 (6H, dd, J 1, 6.5 Hz), 1.32(3H, d, J, 6.5 Hz), 2.05(1H, sept., J 6.5 Hz), 2.82(2H, q, J, 6.5 Hz), 2.92(2H, t, J 8.5 Hz), 3.19(1H, q, J 6.5 Hz), 3.38(1H, q, J 8.5 Hz), 3.54(3H, m), 6.75(1H, dd, J, 1.5, 7.5 Hz), 6.82(1H, d, J 1.5 Hz), 6.99(1H, d, J 7.5 Hz). |
| 57 | 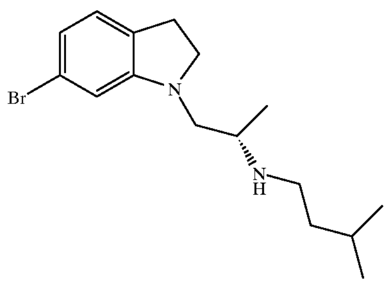 | HCl. mp 161–163° C.; NMR δ$_H$ (400 MHz, DMSO-d$_6$) 0.91 (6H, dd, J, 1, 6.5 Hz), 1.31(3H, d, J 6.5 Hz), 1.56(2H, m), 1.65(1H, sept, J 6.5 Hz), 2.92(4H, m), 3.16(1H, dt, J 5, 17.5 Hz), 3.47(1H, q, J 9 Hz), 3.49(1H, m), 3.53(2H, m), 6.75(1H, dd, J, 1.5, 7.5 Hz), 6.82(1H, d, J 1.5 Hz), 6.99 (1H, J 7.5 Hz). |
| 58 | 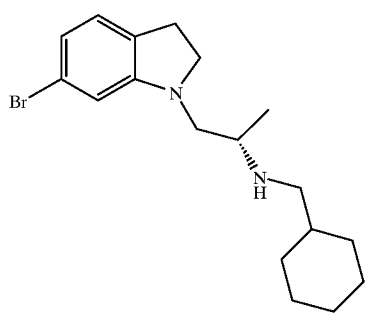 | 2HCl. mp 208–210° C.; NMR δ$_H$ (400 MHz, DMSO-d$_6$) 0.98 (2H, m), 1.20(3H, m), 1.30(3H, d, J 6.5 Hz), 1.71(6H, m), 2.81(2H, q, J 6.5 Hz), 2.91(2H, t, J 8.5 Hz), 3.16(1H, dd, J 6, 13 Hz), 3.39(1H, q, J 8.5 Hz), 3.51(3H, m), 6.75(1H, dd, J 1.5, 75 Hz), 6.82(1H, d, J 1.5 Hz), 6.99(1H, d, J 7.5 Hz). |
| 59 | 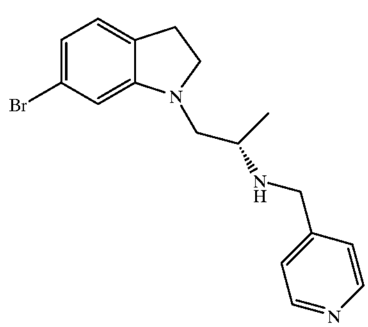 | 2HCl .mp 202–204° C.; NMR δ$_H$ (400 MHz, DMSO-d$_6$) 1.42 (3H, d, J 6.5 Hz), 2.92(2H, m), 3.24(1H, dd, J 6.5, 14 Hz), 3.38(1H, q, J 9 Hz), 3.54(2H, m), 3.68(1H, q, J 7 Hz), 4.47(1H, d, J 14 Hz), 4.58(1H, d, J 14 Hz), 6.76(1H, dd, J, 2, 8 Hz), 6.86(1H, d, J 2 Hz), 6.99(1H, d, J 8 Hz), 8.21 (2H, d, J 6.5 Hz), 8.94(2H, d, J 6.5 Hz). |

Example 60

(S)-1-(5-Fluoro-6-trifluoromethylindolin-1-yl)-2-propylamine Fumarate

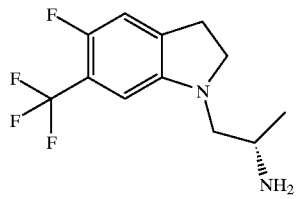

4-Fluoro-3-iodo-6-methylnitrobenzene

A solution of sodium nitrite (3.6 g) in water (20 mL) was added dropwise over 10 min to a stirred suspension of 2-fluoro-4-methyl-5-nitroaniline (8.5 g, 50 mmol) in concentrated hydrochloric acid (100 mL) at 0° C. After a further 20 min at 0° C. the mixture-was added over 5 min to a solution of potassium iodide (9.1 g, 55 mmol) in water (30 mL) keeping the internal temperature below 20° C. After complete addition, the mixture was warmed to room temperature and stirred for 2 h then poured into water (500 mL) and extracted with ether (3×200 mL). The combined organic extracts were washed with saturated aqueous sodium thiosulfate solution (500 mL), dried (magnesium sulfate), filtered and concentrated in vacuo to leave the product as an orange oil. (400 MHz; CDCl$_3$) $\delta_H$ 8.41 (1H, d, J 6 Hz), 7.02 (1H, d, J 8 Hz), 2.59 (3H, s); GC (25 m Quartz/Bonded Phase I; Injection Temperature 250° C.; Detector Temperature 320° C.; Temperature Ramp Rate: 100 to 320° C. at 10° C./min; Carrier Gas Helium; Flow Rate 12 mL/min) Retention Time: 5.92 min.

5-Fluoro-6-iodoindole

N,N-Dimethylformamide dimethylacetal (16.5 mL, 125 mmol) was added in one portion to a stirred solution of 4-fluoro-3-iodo-6-methylnitrobenzene (14.1 g, 50 mmol) in N,N-dimethylformamide (50 mL) at 130° C. under Ar. The mixture was stirred at 130° C. for 10 min then another aliquot of N,N-dimethylformamide dimethylacetal (10 mL) was added in one portion. The mixture was stirred at 130° C. for a further 10 min then another aliquot of N,-dimethylformamide (6 mL) was added in one portion. The mixture was stirred at 130° C. for 10 min then poured into water (400 mL) and extracted with ethyl acetate (3×150 mL). The combined organic extracts were washed with water (200 mL) and brine (200 mL) then dried (magnesium sulfate), filtered and concentrated in vacuo to leave a solid. The solid was dissolved in acetic acid, ethanol (1:1; 240 mL) and iron powder (33.2 g, 600 mmol) was added in one portion. The mixture was placed under an atmosphere of Ar, heated to 90° C. and stirred for 15 min (CARE: VIGOROUS REACTION—COOLING MAY BE REQUIRED). After cooling to room temperature the mixture was filtered through celite and the filtrate was concentrated in vacuo to leave a crude oil. The oil was purified by column chromatography [SiO$_2$; dichloromethane, heptane (1:4 to 2:3)] to give the product (4.8 g, 37%, 3 steps from 2-fluoro-4-methyl-5-nitroaniline) as a green oil: NMR $\delta_H$ (400 MHz; CDCl$_3$) 8.18 (1H, br. s), 7.75 (1H, d, J 5 Hz), 7.32 (1H, d, J 8.5 Hz), 7.22–7.23 (1H, m), 6.50–6.52 (1H, m); GC (25 m Quartz/Bonded Phase I; Injection Temperature 250° C.; Detector Temperature 320° C.; Temperature Ramp Rate: 100 to 320° C. at 10° C./min; Carrier Gas Helium; Flow Rate 12 mL/min) Retention Time: 8.65 min.

(S)-1-[2-(tert-Butoxycarbonylamino)propyl]-5-fluoro-6-iodoindole (S)-1-[2-(tert-Butoxycarbonylamino)propyl]-5-fluoro-6-iodoindole was prepared according to General Method B, step (a) using 5-fluoro-6-iodoindole and (S)-2-(tert-butoxycarbonylamino)propane methanesulfonate to give the product (1.0 g, 57%) as a white solid: IR $\nu_{max}$ (Nujol)/cm$^{-1}$ 3360, 2925, 2854, 1682, 1565, 1531, 1460, 1402, 1377, 1366, 1345, 1325, 1292, 1251, 1228, 1204, 1172, 1141, 1119, 1100, 1063, 1030, 974, 893, 859, 850, 812, 747, 721, 709, 655 and 596; $\delta_H$ (400 MHz; CDCl$_3$) 7.72 (1H, d, J 4.5 Hz), 7.27 (1H, d, J 8.6 Hz), 7.06 (1H, d, J 3.5 Hz), 6.42 (1H, d, J 3.5 Hz), 4.36 (1H, br. s), 3.97–4.20 (3H, m), 1.41 (9H, s), 1.10 (3H, d, J 6.5 Hz).

(S)-1-[2-(tert-Butoxycarbonylamino)propyl]-5-fluoro-6-trifluoromethylindole Methyl 2-chloro-2,2-difluoroacetate (3.0 ml, 28 mmol) was added in one portion to a stirred suspension of (S)-1-[2-(tert-butoxycarbonylamino)propyl]-5-fluoro-6-iodoindole (0.6 g, 1.4 mmol), copper(I)iodide (2.8 g, 14 mmol) and potassium fluoride (0.86 g, 14 mmol) in N,N-dimethylformamide (10 mL) under Ar. The mixture was heated to 120° C. and stirred for 2 h then poured into ethyl acetate (100 mL) and filtered through celite. The filtrate was concentrated in vacuo and purified by column chromatography [SiO$_2$; ethyl acetate-heptane (1:9)] to give the product (0.44 g, 84%) as a white solid: $\delta_H$ (400 MHz; CDCl$_3$) 7.62 (1H, m), 7.33 (1H, d, J 11 Hz), 7.23 (1H, d, J 3.0 Hz), 6.50 (1H, d, J 3.0 Hz), 4.37 (1H, br. s), 3.99–4.27 (3H, m), 1.37 (9H, s), 1.11 (3H, d, J 6.5 Hz); HPLC (Column: Supelcosil ABZ$^+$ [170 mm×4.6 mm], particle size 5 $\mu$M; Eluent: methanol, 10 mM aqueous ammonium acetate solution (4:1); Flow Rate 1.0 mL/min; Detection Wavelength $\lambda$=230 nM) Retention Time: 3.91 min.

(S)-1-[2-(tert-Butoxycarbonylamino)propyl]-5-fluoro-6-trifluoromethylindoline (S)-1-[2-(tert-Butoxycarbonylamino)propyl]-5-fluoro-6-trifluoromethylindoline was prepared according to General Method B, step (b) using (S)-1-[2-(tert-butoxycarbonylamino)propyl]-5-fluoro-6-trifluoromethylindole as a white solid (0.25 g, 45% yield): IR $\nu_{max}$ (Nujol)/cm$^{-1}$ 6785, 3332, 2924, 2854, 1698, 1681, 1645, 1626, 1604, 1540, 1505, 1460, 1440, 1378, 1363, 1345, 1302, 1285, 1264, 1236, 1203, 1158, 1124, 1058, 1034, 1022, 984, 890, 870, 849, 799, 778, 751, 727 and 675; $\delta_H$ (400 MHz; CDCl$_3$) 6.85 (1H, d, J 9.6 Hz), 6.48 (1H, d, J 5 Hz), 4.45 (1H, br. s), 3.84–3.97 (1H, m), 3.48 (1H, dd, J 16.5 Hz, 8.7 Hz), 3.40 (1H, dd, J 16.5 Hz, 8.3 Hz), 2.95–3.04 (4H, m), 1.39 (9H, s), 1.19 (3H, d, J 6.9 Hz).

(S)-1-(5-Fluoro-6-trifluoromethylindolin-1-yl)-2-propylamine Fumarate (S)-1-(5-Fluoro-6-trifluoromethylindolin-1-yl)-2-propylamine fumarate was prepared according to General Method B, step (c) using (S)-1-[2-(tert-butoxycarbonylamino)propyl]-5-fluoro-6-trifluoromethylindoline as a white solid (0.08 g, 35%): mp 190–192° C.; IR $\nu_{max}$ (Nujol)/cm$^{-1}$ 2923, 2854, 2535, 1710, 1627, 1501, 1454, 1398, 1378, 1346, 1285, 1234, 1162, 1121, 1041, 976, 877, 847, 798, 728, 652 and 590; $\delta_H$ (400 MHz, DMSO-d$_6$) 7.19 (1H, d, J 10.1 Hz), 6.81 (1H, d, J 5.4 Hz), 6.44 (2H, s), 3.59–3.63 (1H, m), 3.28–3.38 (3H, m), 2.91–3.06 (3H, m), 1.23 (3H, d, J 5.55 Hz).

Example 61
(S)-1-(5-Fluoro-6-iodoindolin-1-yl)-2-propylamine Fumarate

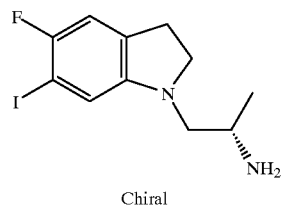
Chiral (S)-1-[2-(tert-Butoxycarbonylamino)propyl)-5-fluoro-6-iodoindoline (S)-1-[2-(tert-Butoxycarbonylamino)propyl)-5-fluoro-6-iodoindoline was prepared according to General Method B. step (b) using (S)-1-[2-(tert-butoxycarbonylamino)propyl)-5-fluoro-6-iodoindole as a white solid (1.6 g, 78%): IR $v_{max}$ (Nujol)/cm$^{-1}$ 3343, 2925, 2854, 1698, 1679, 1646, 1604, 1583, 1535, 1498, 1469, 1405, 1390, 1378, 1363, 1291, 1265, 1253, 1228, 1172, 1129, 1113, 1053, 1034, 1016, 973, 954, 929, 892, 875, 850, 820, 776, 750, 726, 644, 598 and 593; NMR $\delta_H$ (400 MHz; CDCl$_3$) 6.77 (1H, d, J 7.2 Hz), 6.67 (1H, d, J 4.9 Hz), 4.48 (1H, br. s), 3.81–3.93 (1H, m), 3.39–3.48 (2H, m), 2.91–2.99 (4H, m), 1.43 (9H, s), 1.20 (3H, d, J 6.9 Hz).

(S)-1-(5-Fluoro-6-iodoindolin-1-yl)-2-propylamine Fumarate (S)-1-(5-Fluoro-6-iodoindolin-1-yl)-2-propylamine fumarate was prepared according to General Method B, step (c) using (S)-1-[2-(tert-butoxycarbonylamino)propyl)-5-fluoro-6iodoindoline as a white solid (0.12 g, 55%): mp 185–187° C.; IR $v_{max}$ (Nujol)/cm$^{-1}$ 3432, 3199, 2925, 2855, 2538, 1971, 1695, 1657, 1626, 1561, 1487, 1466, 1402, 1377, 1365, 1292, 1255, 1224, 1203, 1178, 1132, 1087, 1045, 1011, 980, 958, 944, 896, 859, 794, 735 and 647; NMR $\delta_H$ (400 MHz; DMSO-d$_6$) 6.99 (1H, d, J 8.2 Hz), 6.92 (1H, d, J 5.0 Hz), 6.46 (2H, s), 3.51–3.53 (1H, m), 3.21–3.31 (3H, m), 2.88–3.02 (3H, m), 1.22 (3H, d, J 6.5 Hz).

Example 62
(S)-1-(5-Fluoro-6-methylindolin-1-yl)-2-propylamine Fumarate

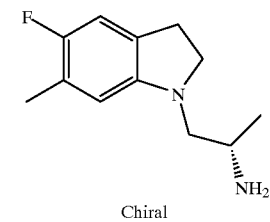
Chiral (S)-1-[2-(tert-Butoxycarbonylamino)propyl]-5-fluoro-6-methylindoline Triphenylphosphine (66 mg, 0.2 mmol) was added in one portion to a stirred solution of palladium(II) acetate (18 mg, 0.06 mmol) in tetrahydrofuran (2.5 mL) under Ar. The mixture was stirred for 5 min then a solution of (S)-1-[2-(tert-butoxycarbonylamino)propyl)-5-fluoro-6-iodoindoline (0.45 g, 1.1 mmol) in tetrahydrofuran (7.5 mL) was added in one portion. The mixture was stirred for 10 min then tetramethyltin (2.0 g, 11 mmol) was added in one portion. The mixture was heated to reflux and stirred for 168 h. After cooling to room temperature, the mixture was poured into an aqueous solution of potassium fluoride (50 mL) and extracted with ethyl acetate (2×30 mL). The combined organic extracts were dried (magnesium sulfate), filtered and concentrated in vacuo to leave a crude oil. The oil was purified by column chromatography [SiO$_2$; ethyl acetate-heptane (1:19)] to give the product (0.17 g, 50%) as a yellow solid; NMR $\delta_H$ (400 MHz, CDCl$_3$) 6.74 (1H, d, J 9 Hz), 6.22 (1H, d, J 5.9 Hz), 4.57 (1H, br. s), 3.82–3.91 (1H, m), 3.31–3.40 (2H, m), 2.89–2.99 (4H, m), 2.05 (3H, s), 1.44 (9H, s), 1.22 (3H, d, J 6.5 Hz).

(S)-1-(5-Fluoro-6-methylindolin-1-yl)-2-propylamine Fumarate (S)-1-(5-Fluoro-6-methylindolin-1-yl)-2-propylamine fumarate was prepared according to General Method B, step (c) using (S)-1-[2-(tert-butoxycarbonylamino)propyl]-5-fluoro-6-methylindoline as a solid (0.08 g, 50%): LC Supelcosil ABZ$^+$ (170 mm×4.6 mm: particle size 5 μm), methanol/10 mM aqueous ammonium acetate, flow rate of 1.0 mL/min, $\lambda_{det}$=254 nm, retention time=2.64 min; NMR $\delta_H$ (400 MHz; DMSO) 6.86 (1H, d, J 9.5 Hz), 6.51 (2H, s), 6.45 (1H, d, J 6.7 Hz), 3.38–3.49 (1H, m), 3.19–3.27 (3H, m), 2.85–3.00 (3H, m), 2.15 (3H, s), 1.24 (3H, d, J 6.5 Hz).

Example 63
(S)-1-[6-(4-Hydroxytetrahydrothiopyran-4-yl)indolin-1-yl)-2-propylamine Fumarate

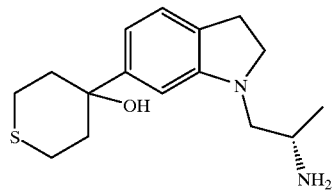

(S)-1-[2-(tert-Butoxycarbonylamino)propyl]-6-(4-hydroxytetrahydrothiopyran-4-yl)indoline To a stirred suspension of potassium hydride (30% dispersion in mineral oil, 0.08 g, 0.60 mmol) in dry tetrahydrofuran (2 mL) at 0° C., under argon, was added a solution of (S)-1-[2-(tert-butoxycarbonylamino)propyl]-6-bromoindoline (0.20 g, 0.60 mmol) in tetrahydrofuran (1 mL). After 15 mins, the solution was cooled to −78° C. and tert-butyl lithium (1.7 M, 0.68 mL, 1.2 mmol) was added dropwise. The mixture was stirred for a further 45 mins and then tetrahydrothiopyran-4-one (0.14 g, 1.2 mmol) was added portionwise. The solution was warmed gradually to room temperature, then diluted carefully with saturated ammonium chloride solution (10 mL). The mixture was extracted with ether (2×10 mL). The extracts were dried (magnesium sulfate), evaporated in vacuo and purified by column chromatography [SiO$_2$; heptane-ethyl acetate (2:1)] to give the product (0.20 g, 90%). $\delta_H$ (400 MHz, CDCl$_3$) 0.88 (2H, t, J 7 Hz), 1.24 (3H, d, J 6.5 Hz), 1.42 (9H, s), 1.99 (1H, m), 2.03 (1H, m), 2.13–2.21 (2H, m), 2.44 (1H, m), 2.48 (1H, m), 2.99 (2H, t, J 9 Hz), 3.06 (1H, dd, J 5.5, 13.5 Hz), 3.22 (2H, dt, J 2.5, 9 Hz), 3.50 (2H, m), 3.94 (1H, m), 6.79 (2H, m), 7.07 (1H, J 7.5 Hz); BPLC (Column: Supelcosil ABZ$^+$ [170 mm×4.6 mm], particle size 5 μM; Eluent: methanol, 10 mM aqueous ammonium acetate solution (4:1); Flow Rate 1.0 mL/min; Detection Wavelength $\lambda$=230 nM) Retention Time: 3.51 min.

63

(S)-1-[6-(4-Hydroxytetrahydrothiopyran-4-yl)indolin-1-yl)-2-propylamine Fumarate (S)-1-[6-(4-Hydroxytetrahydrothiopyran-4-yl)indolin-1-yl)-2-propylamine fumarate was prepared according to General Method B, step (c) using (S)-1-[2-(tert-butoxycarbonylamino)propyl]-6-(4-hydroxytetrahydrothiopyran-4-yl)indoline to give the product as a white solid (0.056 g, 51%). NMR $\delta_H$ (400 MHz, DMSO-$d_6$) 1.25 (3H, d, J 6.5 Hz), 1.81 (2H, m), 1.97 (2H, m), 2.36 (2H, m), 2.82 (1H, t J 6 Hz), 2.89 (2H, m), 2.99 (1H, dd, J 5.5, 14 Hz), 3.09 (2H, dt, J 2, 9 Hz), 3.27 (1H, m), 3.40 (1H, m), 3.47 (1H, m), 6.44 (2H, s), 6.72 (1H, brs), 6.74 (1H, dd, J 1.5, 7.5 Hz), 6.99 (1H, d, J 7.5 Hz); HPLC (Column: Supelcosil ABZ$^+$ [170 mm×4.6 mm], particle size 5 μM; Eluent: methanol, 10 mM aqueous ammonium acetate solution (7:3); Flow Rate 1.0 mL/min; Detection Wavelength λ=210 nM) Retention Time: 3.40 min.

Example 64
(S)-1-(6-Methylindolin-1-yl)-2-propylamine Fumarate

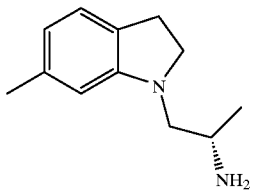

(S)-1-2-(tert-Butoxycarbonylamino)propyl]-6-methylindoline

To a stirred suspension of palladium(II)acetate (0.012 g, 0.05 mmol) in THF (5 mL) under Ar was added triphenylphosphine (0.058 g, 0.22 mmol). The mixture was stirred for 10 min and (S)-1-[2-(tert-butoxycarbonylamino)propyl]-6-bromoindoline (0.39 g, 1.1 mmol) was added. The mixture was stirred for 10 min and methylboronic acid (0.13 g, 2.20 mmol) in ethanol (2 mL) followed by aqueous sodium bicarbonate solution (2M, 5 mL, 10 mmol) were added. The mixture was heated to reflux for 16 h, cooled to room temperature and partitioned between ether (25 mL) and water (2×25 mL). The organic layer was washed with brine, dried (magnesium sulfate), concentrated in vacuo and purified by column chromatography [SiO$_2$, heptane, ether (3:1)] to give the product as a white solid (0.07 g, 22%). $\delta_H$ (400 M, CDCl$_3$) 1.23 ((3H, d, J 6.5 Hz), 1.44 (9H, s), 2.28 (3H, s), 2.93 (2H, t, J 8.5 Hz), 3.04 (2H, m), 3.40 (2H, m), 6.30 (1H, s), 6.48 (1H, d, J 7.5 Hz), 6.96 (1H, d, J 7.5 Hz), (contains 25% des-methyl); HPLC (Column: Supelcosil ABZ$^+$ [170 mm×4.6 mm], particle size 5 μM; Eluent: methanol, 10 mM aqueous ammonium acetate solution (4:1); Flow Rate 1.0 mL/min; Detection Wavelength λ=230 nM) Retention Time: 4.18 min.

(S)-1-(6-Methylindolin-1-yl)-2-propylamine Fumarate (S)-1-(6-Methylindolin-1-yl)-2-propylamine fumarate was prepared according to General Method B, step (c) using (S)-1-[2-(tert-butoxycarbonylamino)propyl]-6-methylindoline to give the product as a white solid (0.053 g, 79%). $\delta_H$ (400 MHz, DMSO-$d_6$) 1.23 (3H, d, J 6.5 Hz), 2.21 (3H, s), 2.86 (2H, m), 2.97 (1H, m), 3.00 (1H, dd, J 5.5, 14 Hz), 3.24 (2H, m), 3.40 (1H, m), 6.45 (2H, s), 6.60 (1H, t, J 8 Hz), 6.94 (1H, d, J 7.5 Hz), 7.06 (1H, d, J 7.5 Hz) (contains 25% des-methyl); HPLC (Column: Supelcosil ABZ$^+$ [170 mm×4.6 mm], particle size 5 μM; Eluent: methanol, 10 mM aqueous ammonium acetate solution (7:3); Flow Rate 1.0 mL/min; Detection Wavelength λ=210 nM) Retention Time: 2.49 min.

What is claimed is:

1. A compound of formula (I):

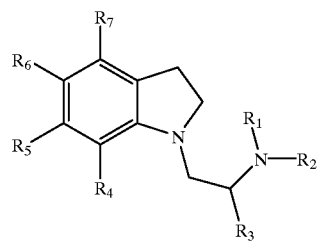

(I)

wherein:
$R_1$ to $R_3$ are independently selected from hydrogen and alkyl;
$R_4$ to $R_7$ are independently selected from hydrogen, halogen, hydroxy, alkyl, aryl, heterocycle, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, wherein at least one of $R_4$ to $R_7$ is a substituent group other than hydrogen, and pharmaceutically acceptable salts and prodrugs thereof; and
wherein $R_7$ is selected from a group other than hydroxy and wherein the compound is other than 2,3-dihydro-1-(2-dimethylaminoethyl)-6-nitro-1H-indote or 6-amino-2,3-dihydro-1-(2-dimethylaminoethyl)1H-indote.

2. A compound according to claim 1 wherein $R_7$ is hydrogen.

3. A pharmaceutical composition comprising a chemical compound of formula (I):

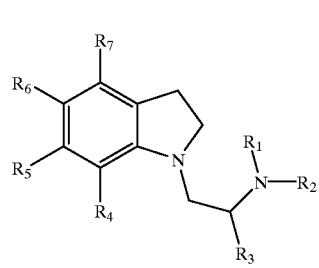

(I)

wherein:
$R_1$ to $R_3$ are independently selected from hydrogen and alkyl;
$R_4$ to $R_7$ are independently selected from hydrogen, halogen, hydroxy, alkyl, aryl, heterocyclyl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, wherein at least one of $R_4$ to $R_7$ is a substituent group other than hydrogen, and pharmaceutically acceptable salts and prodrugs thereof; and a pharmaceutically acceptable carrier.

4. A composition according to claim 3 wherein $R_1$ and $R_2$ are hydrogen.

5. A composition according to claim 3 wherein $R_1$ is hydrogen and $R_2$ is alkyl.

6. A composition according to claim 3 wherein $R_1$ is hydrogen and $R_2$ is arylalkyl.

7. A composition according to claim 3, wherein $R_3$ is alkyl.

8. A composition according to claim 3, wherein $R_3$ is methyl.

9. A composition according to claim 3 wherein $R_4$ is hydrogen or halogen.

10. A composition according to claim 3 wherein $R_5$ is selected from halogen, alkyl, aryl, alkoxy, alkylthio, monoalkylamino and dialkylamino.

11. A composition according to claim 3 wherein $R_5$ is selected from alkylthio.

12. A composition according to claim 3 wherein $R_6$ is selected from halogen and hydrogen.

13. A composition according to claim 3 wherein $R_7$ is hydrogen.

14. A composition according to claim 3 wherein the compounds of formula (I) are selected from the group consisting of 1-(6-chloro-5-fluoroindolin-1-yl)-2-propylamine, 1-(5,6-difluoroindolin-1-yl)-2-propylamine, 1-(6-bromo-5-fluoroindolin-1-yl)-2-propylamine, 1-(6-bromoindolin-1-yl)-2-propylamine, 1-(6-chloroindolin-1-yl)-2-propylamine, 1-(5-fluoro-6-trifluoromethylindolin-1-yl)-2-propylamine, 1-(5-fluoro-6-methylthioindolin-1-yl)-2-propylamine, 1-(5-fluoro-6-iodoindolin-1-yl)-2-propylamine, 1-(5-fluoro-6-ethylthioindolin-1-yl)-2-propylamine, 1-(-5-fluoro-6-methylindolin-1-yl)-2-propylamine, 1-(6-methylthioindolin-1-yl)-2-propylamine, 1-(6-ethylthioindolin-1-yl)2-propylamine, 1-(6-trifluoromethylindolin-1-yl)-2-propylamine, 1-(6-methoxyindolin-1-yl)-2-propylamine, 1-(6-propylthioindolin-1-yl)-2-propylamine, 1-(6-isopropylthioindolin-1-yl)-2-propylamine, 2-(6-chloroindolin-1-yl)-1-ethylamine, 2-(6-bromoindolin-1-yl)-1-ethylamine, 1-(5-chloroindolin-1-yl)-2-propylamine, 1-(5-fluoroindolin-1yl)-2-propylamine and 1-(6-methylindolin-1-yl)-2-propylamine.

15. A composition according to claim 3, wherein the compounds are selected from the (S)-enantiomers thereof.

16. A method of treatment of disorders of the central nervous system; damage to the central nervous system; cardiovascular disorders; gastrointestinal disorders; diabetes insipidus, and sleep apnea, comprising administering to a patient in need of such treatment an effective dose of a composition as set out in claim 3.

17. A method according to claim 16 wherein the disorders of the central nervous system are selected from the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addition, obesity, bulimia, anorexia nervosa and premenstrual tension.

18. A method according to claim 16 wherein the damage to the central nervous system is by trauma, stroke, neurodegenerative diseases or toxic or infective CNS diseases.

19. A method according to claim 18 wherein said toxic or infective CNS disease is encephalitis or meningitis.

20. A method according to claim 16 wherein the cardiovascular disorder is thrombosis.

21. A method according to claim 16 wherein the gastrointestinal disorder is dysfunction of gastrointestinal motility.

22. A method according to claim 16 wherein said medicament is for the treatment of obesity.

23. A method according to claim 16 wherein said treatment is prophylactic treatment.

* * * * *